US005776962A

United States Patent [19]
Gross et al.

[11] Patent Number: 5,776,962
[45] Date of Patent: *Jul. 7, 1998

[54] LACTONE COMPOUNDS FOR TREATING PATIENT WITH PRECANCEROUS LESIONS

[75] Inventors: Paul Gross; Gerhard Sperl. both of Stockton. Calif.; Rifat Pamukcu. Spring House. Pa.; Klaus Brendel. Tucson. Ariz.

[73] Assignees: Cell Pathways, Inc.. Aurora. Colo.; University of Arizona. Tucson. Ariz.

[*] Notice: The term of this patent shall not extend beyond the expiration date of Pat. No. 5,696,159.

[21] Appl. No.: 481,601

[22] Filed: Jun. 7, 1995

Related U.S. Application Data

[63] Continuation-in-part of Ser. No. 265,396, Aug. 3, 1994.
[51] Int. Cl.⁶ .......................... A61K 31/41; C07D 307/77
[52] U.S. Cl. .......................... 514/359; 514/410; 514/411; 514/468; 549/298; 549/299; 548/262.4; 548/422; 548/431; 548/961
[58] Field of Search ...................... 549/298, 299; 548/262.4, 422, 431, 961; 514/359, 410, 411, 468

[56] References Cited

U.S. PATENT DOCUMENTS

| | | | |
|---|---|---|---|
| 3,031,450 | 4/1962 | Fischer et al. | 260/247.5 |
| 3,161,654 | 12/1964 | Shen | 260/319 |
| 3,322,755 | 5/1967 | Roch et al. | 260/246 |
| 3,517,005 | 6/1970 | Cronin et al. | 260/256.4 |
| 3,594,480 | 7/1971 | Cronin et al. | 424/250 |
| 3,647,858 | 3/1972 | Hinkley et al. | 260/470 |
| 3,654,349 | 4/1972 | Shen et al. | 260/515 |
| 3,780,040 | 12/1973 | Schnettler et al. | 260/256.5 |
| 3,812,127 | 5/1974 | Cronin et al. | 260/268 BQ |
| 3,819,631 | 6/1974 | Broughton et al. | 260/256.4 F |
| 3,920,636 | 11/1975 | Takahasi et al. | 260/240 J |
| 4,001,237 | 1/1977 | Partyka et al. | 260/256.4 B |
| 4,001,238 | 1/1977 | Partyka et al. | 260/256.4 B |
| 4,039,544 | 8/1977 | Broughton et al. | 260/256.4 F |
| 4,060,615 | 11/1977 | Matier et al. | 424/251 |
| 4,079,057 | 3/1978 | Juby et al. | 260/256.5 R |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/285 |
| 4,138,561 | 2/1979 | Crenshaw et al. | 544/284 |
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 424/251 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,460,590 | 7/1984 | Möller | 424/251 |
| 4,460,591 | 7/1984 | DeGraw et al. | 424/251 |
| 4,885,301 | 12/1989 | Coates | 514/263 |
| 5,030,646 | 7/1991 | Malen et al. | 514/397 |
| 5,147,875 | 9/1992 | Coates et al. | 514/259 |
| 5,254,571 | 10/1993 | Coates et al. | 514/344 |
| 5,401,774 | 3/1995 | Pamukcu et al. | 514/569 |

FOREIGN PATENT DOCUMENTS

| | | |
|---|---|---|
| 0 347 146 A2 | 12/1989 | European Pat. Off. . |
| 0 349 239 A2 | 1/1990 | European Pat. Off. . |
| 0 351 058 | 1/1990 | European Pat. Off. . |
| 0 352 960 A2 | 1/1990 | European Pat. Off. . |
| 0 395 328 A2 | 10/1990 | European Pat. Off. . |
| 0 428 268 A2 | 5/1991 | European Pat. Off. . |
| 0 463 756 A1 | 1/1992 | European Pat. Off. . |
| 0 485 157 A2 | 5/1992 | European Pat. Off. . |
| 0 485 158 A2 | 5/1992 | European Pat. Off. . |
| 0 485 171 A2 | 5/1992 | European Pat. Off. . |
| 0 485 172 A2 | 5/1992 | European Pat. Off. . |
| 0 485 173 A2 | 5/1992 | European Pat. Off. . |
| 0 508 586 A1 | 10/1992 | European Pat. Off. . |
| 0 526 004 A1 | 2/1993 | European Pat. Off. . |
| 0 607 439 A1 | 7/1994 | European Pat. Off. . |
| 56-53659 A | 5/1981 | Japan . |
| 57-167974 A | 10/1982 | Japan . |
| 807 826 | 1/1959 | United Kingdom . |
| 2063249 A | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |

OTHER PUBLICATIONS

Rosenmund, P. and Sadri, E., "Synthesen eserinähnlicher Verbindungen, III; Neue an N–1 und N–8 substituierte Derivate des Desoxyeserolins sowie eine neue Synthese des Eserthols," *Liebigs Ann. Chem.*, pp. 927–943 (1979). (German Language—No Translation Available).

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1993).

Gilman, S.C. et al., Nonsteroidal Anti–inflammatory Drugs in Cancer Therapy, (circa 1985) p. 157.

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavan, G.B. et al., Toxicology and Applied Pharmacology, vol. 83, pp. 386–389 (1986).

Moorghen, M. et al., Journal of Pathology, vol. 156, pp.
Moorghen, M. et al., Acta Histochemica, Suppl.-Band XXIX, S. 195–199 (1990), 341–347 (1988).

(List continued on next page.)

*Primary Examiner*—Amelia Owens
*Attorney, Agent, or Firm*—Brinks Hofer Gilson & Lione

[57] ABSTRACT

Substituted lactone compounds are useful in the treatment of precancerous lesions and neoplasms.

43 Claims, No Drawings

OTHER PUBLICATIONS

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of Nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N. c. et al., Relaxation of guinea–pig trachea by cyclic AMP phosphodiesterase and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem, Pharmacology, vol.35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem., Pharmacology, vol. 46, No. 5, pp. 833–839 (1993).

Turner, N. C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3", 5"–Monophosphate,J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073–2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Adminstration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibiton of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purfied Human Lung Tissue Adenosine Cyclic 3', 5'–Monophosphate and Guanosine Cyclic 3', 5'–Monophosphate Phosphodiesterases, Molecular Pharmacology, 13, pp. 38–43 (1976).

Drees, Markus et al., 3', 5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 50–525 (1993).

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2) pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, Sep. 26, 1991.

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibiton in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

LACTONE COMPOUNDS FOR TREATING PATIENT WITH PRECANCEROUS LESIONS

RELATED APPLICATIONS

This application is a continuation-in-part of application Ser. No. 08/265,396 filed on Aug. 3, 1994.

TECHNICAL FIELD

This invention relates to compounds and methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those with high risk genetic factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Unfortunately, most chemotherapeutic drugs have serious side effects that prohibit their long term use, or use in otherwise healthy individuals with precancerous lesions. These side effects, which are a result of the high levels of cyto-toxicity of the drugs, include hair loss, weight loss, vomiting and bone marrow immune suppression. Therefore, there is a need to identify new drug candidates for therapy that do not have such serious side effects in humans.

Recently, several non-steroidal anti-inflammatory drugs ("NSAIDs"), originally developed to treat arthritis, have shown effectiveness in inhibiting and eliminating the polyps. Polyps virtually disappear when the patient take the drug, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive an antiarthritic agent. The sulfoxide is reported to be converted by liver enzymes to the corresponding sulfide, which is acknowledged to be the active moiety as a prostaglandin inhibitor. The sulfide, however, is associated with the side effects of conventional NSAIDs. The sulfoxide is also known to be metabolized to sulfone compound, which is regarded to be inactive as an inhibitor of prostaglandin synthesis.

SUMMARY OF THE INVENTION

This invention includes compounds and a method of treating patients with precancerous lesions by administering a physiologically effective amount of those compounds described below to a patient in need of such treatment. Such compositions are effective in eliminating and inhibiting the growth of precancerous lesions and neoplasms, but are not characterized by the severe side reactions of conventional NSAIDs.

The compounds used in the treatment of this invention are believed to be effective on precancerous lesions either because they are active themselves or because they are metabolized to active derivatives.

It was unexpectedly discovered that while the compounds of this invention do not greatly inhibit prostaglandin synthesis—prostaglandin synthesis inhibition being a characteristic of conventional NSAIDs—the compounds of this invention nonetheless have antiproliferative effects on precancerous lesion cells.

DETAILED DESCRIPTION OF THE INVENTION

As discussed above, the present invention includes the compounds below for treating a patient with precancerous lesions:

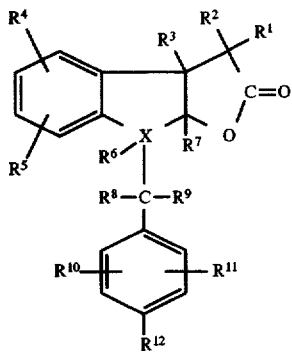

X can be carbon, or $R^6$—X equals nitrogen.

$R_1$ and $R_2$ are independently selected from the group consisting of hydrogen, amino, lower alkyl, lower alkoxy, azide, hydroxy, halogen, acetoxyl, benzoxyl, or substituted phenyl where the substituents are selected from the group consisting of halogen, lower alkyl, or lower alkoxy; or $R_1$ and $R_2$ form a carbonyl or imine; or $R_2$ and $R_3$ together form a double bond, aziridin, epoxide or triazole; or a dioxolane.

$R_3$ is selected from the group consisting of hydrogen, halogen, azide, lower alkyl, lower alkoxy, di(lower)alkyl amino(lower)alkoxy, cyano, hydroxy, di(lower)alkyl amino (lower)alkylthio, loweralkylthio, phenylthio, or di(lower) alkyl amino. $R_3$ is further selected from a group of sulfur containing acids and peptides, which are coupled by their thio group. Preferred compounds are mercaptoacetic acid, cysteine, N—Ac-cysteine and glutathione.

$R_4$ is selected from the group consisting of hydrogen, hydroxy, halogen, lower alkoxy or lower alkyl, or lower dialkyl amino.

$R_5$ is selected from the group consisting of hydrogen, hydroxy, halogen, lower alkoxy, lower alkyl, amino, or lower dialkyl amino.

$R_6$ is selected from the group consisting of hydrogen, lower alkyl, hydroxy, lower alkoxy, halogen or $R_6$ and $R_8$ together from a double bond.

$R_7$ is selected from the group consisting of hydrogen, lower alkyl, phenyl, halo(lower)alkyl, hydroxy(lower)alkyl, acetoxy(lower)alkyl, benzyloxy(lower)alkyl, or (lower) alkyl(lower)alkoxy, or (lower)dialkylamino(lower)alkyl.

$R_8$ and $R_9$ are independently selected from the group consisting of hydrogen, lower alkyl, hydroxy, lower alkoxy, or halogen; or $R_8$ & $R_9$ together may be oxygen.

$R_{10}$ and $R_{11}$ are independently selected from the group consisting of hydrogen, halogen, lower alkoxy, or lower alkyl.

$R_{12}$ is selected from the group consisting of hydrogen, halogen, lower alkyl, lower alkoxy, loweralkylthio, loweralkylsulfinyl, lower alkyl sulfonyl, or amidosulfonyl.

Preferred compounds of this invention include those when X is carbon where $R_1$ and $R_2$ are independently selected from the group consisting of hydrogen, amino, lower alkyl, lower alkoxy, azide, hydroxy, or halogen, or $R_1$ and $R_2$ form a carbonyl; or $R_2$ and $R_3$ form a double bond, aziridin, epoxide, triazole or dioxolane;

$R_4$ and $R_5$ are selected from the group consisting of hydrogen, halogen or lower alkoxy;

$R_6$ is hydrogen or together with $R_8$ forms a double bond;

$R_7$ is selected from the group consisting of hydrogen, lower alkyl, halo(lower)alkyl, hydroxy(lower)alkyl, acetoxy (lower)alkyl, benzyloxy(lower)alkyl, or (lower)alkyl(lower) alkoxy; and $R_8$–$R_{11}$ are hydrogen.

When X is nitrogen, preferred compounds of this invention include those where $R_1$ and $R_2$ are independently selected from the group consisting of hydrogen, amino, lower alkyl, lower alkoxy, azide, hydroxy, or halogen, or $R_1$ and $R_2$ form a carbonyl; or $R_2$ and $R_3$ form a double bond, aziridin, epoxide, triazole or dioxolane;

$R_4$ and $R_5$ are independently selected from the group consisting of hydrogen, halogen or lower alkoxy;

$R_7$ is selected from the group consisting of hydrogen, lower alkyl, halo(lower)alkyl, hydroxy(lower)alkyl, acetoxy (lower)alkyl, benzyloxy(lower)alkyl, or (lower)alkyl(lower) alkoxy;

$R_8$ and $R_9$ together are an oxygen; and $R_{10}$–$R_{11}$ are hydrogen.

The present invention also is a method of treating a patient with precancerous lesions by administering a physiologically effective amount of the following compounds (preferably in the absence of an NSAID) to a patient in need of such treatment:

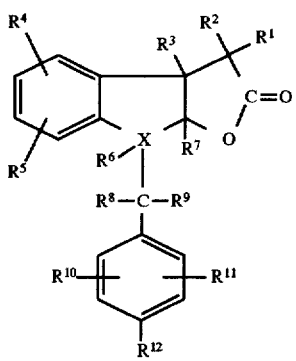

X can be carbon, or $R^6$—X equals nitrogen.

$R_1$ and $R_2$ are independently selected from the group consisting of hydrogen, amino, lower alkyl, lower alkoxy, azide, hydroxy, halogen, acetoxyl, benzoxyl, or phenyl or substituted phenyl where the substituents are selected from the group consisting of halogen, lower alkyl, or lower alkoxy; or $R_1$ and $R_2$ form a carbonyl or imine; or $R_2$ and $R_3$ together form a double bond, aziridin, epoxide or triazole; or a dioxolane.

$R_3$ is selected from the group consisting of hydrogen, halogen, azide, lower alkyl, lower alkoxy, di(lower)alkyl amino(lower)alkoxy, cyano, hydroxy, di(lower)alkyl amino (lower)alkylthio, loweralkylthio, phenylthio, or di(lower) alkyl amino. $R_3$ is further selected from a group of sulfur containing acids and peptides, which are coupled by their thio group. Preferred compounds are mercaptoacetic acid, cysteine, N—Ac-cysteine and glutathione.

$R_4$ is selected from the group consisting of hydrogen, hydroxy, halogen, lower alkoxy or lower alkyl, or lower dialkyl amino.

$R_5$ is selected from the group consisting of hydrogen, hydroxy, halogen, lower alkoxy, lower alkyl, amino, or lower dialkyl amino.

$R_6$ is selected from the group consisting of hydrogen, lower alkyl, hydroxy, lower alkoxy, halogen or $R_6$ and $R_8$ together from a double bond.

$R_7$ is selected from the group consisting of hydrogen, lower alkyl, phenyl, halo(lower)alkyl, hydroxy(lower)alkyl, acetoxy(lower)alkyl, benzyloxy(lower)alkyl, or (lower) alkyl(lower)alkoxy, or (lower)dialkylamino(lower)alkyl.

$R_8$ and $R_9$ are independently selected from the group consisting of hydrogen, lower alkyl, hydroxy, lower alkoxy, or halogen; or $R_8$ & $R_9$ together may be oxygen.

$R_{10}$ and $R_{11}$ are independently selected from the group consisting of hydrogen, halogen, lower alkoxy, or lower alkyl.

$R_{12}$ is selected from the group consisting of hydrogen, halogen, lower alkyl, lower alkoxy, loweralkylthio, loweralkylsulfinyl, lower alkyl sulfonyl, or amidosulfonyl.

The present invention is also a method of treating individuals with precancerous lesions by administering a pharmaceutically effective amount of an enterically coated compounds of this invention.

As used herein, the term "precancerous lesion" includes syndromes represented by abnormal neoplastic, including dysplastic, changes of tissue. Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, breast and/or skin and related conditions, whether the lesions are clinically identifiable or not.

As used herein, the term "carcinomas" refers to lesions which are cancerous. Examples incloude malignant melanomas, breast cancer, and colon cancer.

As used herein, the term "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups. The term "lower alkyl" refers to $C_1$ to $C_8$ alkyl groups.

Compounds of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of this invention excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

The pharmaceutical compositions of this invention are preferably packaged in a container (e.g. a box or bottle, or both) with suitable printed material (e.g. a package insert) containing indications, directions for use, etc.

In another form, the invention is a method of inhibiting the growth of neoplastic cells by exposing them to an effective amount of the compound of formula [I] above.

The foregoing may be better understood from the following examples, which are presented for purposes of illustration and are not intended to limit the scope of the invention. As used in the following examples, the references to substituents such as R, $R_1$, $R_2$ etc., refer to the corresponding compounds and substituents in the formula I above. In examples 1 through 34, X is carbon.

EXAMPLE 1 rac-threo-(E)-1-Bromo-1-(Butan-1',4'-olido)-|3',4':1, 2|-6-fluoro-2-methyl-3-(p-methylsulfonylbenzylidene-indan (A) p-Fluoro-α-methylcinnamic acid.

p-Fluorobenzaldehyde (200 g, 1.61 mol), propionic anhydride (3.5 g, 2.42 mol) and sodium propionate (155 g, 1.61 mol) are mixed in a 1 l three-necked flask which had been flushed with nitrogen. The flask is heated gradually in an oil-bath to 140°. After 20 h, the flask is cooled to 100°and poured into 8 l of water. The precipitate is dissolved by adding potassium hydroxide (302 g) in 2 l of water. The aqueous solution is extracted with ether, and the ether extracts washed with potassium hydroxide solution. The combined aqueous layers are filtered, are acidified with concentrated HCl, and are filtered. The collected solid, p-fluoro-α-methylcinnamic acid, is washed with water, and is dried and used as obtained.

(B) p-Fluoro-α-methylhydrocinnamic acid.

To p-fluoro-α-methylcinnamic acid (177.9 g, 0.987 mol) in 3.6 l ethanol is added 11.0 g of 5% Pd/C. The mixture is reduced at room temperature under a hydrogen pressure of 40 p.s.i. When hydrogen uptake ceases, the catalyst is filtered off, and the filtrate is concentrated in vacuo to give the product, p-fluoro-α-methylhydrocinnamic acid, which was used without weighing in the next step.

(C) 6-Fluoro-2-methylindanone

To 932 g polyphosphoric acid at 70° C. (on the steam bath) is added p-fluoro-α-methylhydrocinnamic acid (93.2 g, 0.5 mol) slowly with stirring. The temperature is gradually raised to 95° C., and the mixture is kept at this temperature for 1 hour. The mixture is allowed to cool and added to 2 l of water. The aqueous layer is extracted with ether, the ether solution is washed twice with saturated sodium chloride solution, 5% $Na_2CO_3$ solution, water, and is then dried. The ether filtrate is concentrated with 200 g silica-gel, and is added to a five pound silica-gel column packed with 5% ether-petroleum ether. The column is eluted with 5–10% ether-petroleum ether, to give 6-fluoro-2-methylindanone. Elution is followed by TLC.

(D) 5-fluoro-2-methylindanone-3-acetic acid

A mixture of 6-fluoro-2-methylindanone (18.4 g, 0.112 g mol), cyanoacetic acid (10.5 g, 0.123 mol), acetic acid (6.6 g), and ammonium acetate (1.7 g) in dry toluene (15.5 ml) is refluxed with stirring for 21 h, as the liberated water is collected in a Dean Stark trap. The toluene is concentrated, and the residue dissolved in 60 ml of hot ethanol and 14 ml of 2.2N aqueous potassium hydroxide solution. 22 g of 85% KOH in 150 ml of water is added, and the mixture refluxed for 13 h under nitrogen. The ethanol is removed under vacuum, 500 ml water added, the aqueous solution is washed well with ether and then boiled with charcoal. The aqueous filtrate is acidified to pH 2 with 50% cold hydrochloric acid. The precipitate and dried 5-fluoro-2-methylindenyl-3-acetic acid (m.p. 164°–166° C.) is obtained.

(E) 5-fluoro-2-methyl-1-(p-methylthiobenzylidene)-3-indenylacetic acid 5-fluoro-2-methyl-3-indenylacetic acid (15 g, 0.072 mol) p-methylthiobenzaldehyde (14.0 g, 0.091 mol) and sodium methoxide (13.0 g, 0.24 mol) are heated in methanol (200 ml) at 60° under nitrogen with stirring for 6 h. After cooling, the reaction mixture is poured into 750 ml of ice-water, and is acidified with 2.5N hydrochloric acid. The collected solid is triturated with a little ether to produce 5-fluoro-2-methyl-1-(p-methylthiobenzylidene)-3-indenylacetic acid (m.p. 187°–188.2° C.).

(F) 5-fluoro-2-methyl-1-(p-methylsulfinylbenzylidene)-3-indenylacetic acid

To a solution of 5-fluoro-2-methyl-1-(p-methylthiobenzylidene)-3-indenyl acetic acid (3.4 g, 0.01 mol) in a mixture of methanol (250 ml) and acetone (100 ml) is added a solution of sodium periodate (3.8 g, 0.018 mol) in water (50 ml) with stirring.

Water (450 ml) is added after 18 h, and the organic solvents removed under vacuum below 30° C. The precipitated product is filtered, dried and recrystallized from ethyl acetate to give 5-fluoro-2-methyl-1-(p-methylsulfinylbenzylidene)-3-indenylacetic acid. Upon repeated recrystallization upon ethylacetate there is obtained cis-5-fluoro-2-methyl-1-(p-methylsulfinylbenzylidene)-3-indenylacetic acid, m.p. 184°–186° C.

Further runs reveal the existence of a second polymorph of cis-5-fluoro-2-methyl-1-(p-methylsulfinylbenzylidene)-3-indenyl acetic acid, m.p. 179°–181° C.

(G) 5-fluoro-2-methyl-1-(p-methylsulfonylbenzylidene)-3-indenylacetic acid

To 5-fluoro-2-methyl-1-(p-methylsulfinylbenzylidene)-3-indenylacetic acid (12.0 g, 33.66 mmol) in 140 ml THF is added gradually at 0° C. a solution of OXONE (12.47 g, 36.72 mmol) and tetrabutylammoniumhydrogensulfate (1.0 g, 1.62 mmol) in 35 ml $H_2O$. The temperature of the reaction mixture is maintained in the range of 13°–23° C. After 24 h at room temperature, the THF phase is separated from the water phase and is dripped into water (280 ml, 40° C.). The suspension is stirred until it reaches room temperature. The yellow crystals of 5-fluoro-2-methyl-1-(p-methylsulfonylbenzylidene)-3-indenylacetic acid are filtered off and are washed with water (30 ml). 11.3 g, 30.29 mmol, 90% mp. 204°–206° C.

(H) rac-threo-(E)-1-Bromo-1-(butan-1',4'-olido)-|3', 4':1,2|-6-fluoro-2-methyl-3-(p-methylsulfonylbenzylidene)-indan N-Bromosuccinimide (98%, 3×1.76 g, 29.8 mmol) is added to a stirred solution of (Z)-5-fluoro-2-methyl-1-(p-methylsulfonylbenzylidene)-3-indenylacetic acid (10 g, 26.9 mmol) in DMA/$H_2O$ (22 ml, 10:1). After 24 h at room temperature, the resulting suspension is added dropwise to stirred ice-water (1000 ml). A pale yellow precipitate is filtered off, is washed with water (500 ml), and is recrystallized from dichloromethane/n-hexane to give white crystals of rac-threo-(E)-1-Bromo-1-(butan-1',4'-olido)-[3',4':1, 2]-6-fluoro-2-methyl-3-(p-methylsulfonylbenzylidene)-indan (7.3 g, 16.1 mmol, 60%). $C_{20}H_{16}BrFO_4S$:451.31; mp. 195° C.

$R_1$=hydrogen, $R_2$=hydrogen, $R_3$=bromo, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl.

EXAMPLE 2 rac-threo-(E)-1-Bromo-1-(butan-1',4'-olido)-[3',4':1, 2]-6-fluoro-2-methyl-3-(p-methylsulfinylbenzylidene)-indan N-Bromosuccinimide (98%, 0.6 g, 4.4 mmol) is added to a stirred solution of (Z)-5-fluoro-2-methyl-1-(p-methylsulfinylbenzylidene)-3-indenylacetic acid (1 g, 2.8 mmol) in DMA/water (4 ml DMA/0.1 ml water). After 24 h at room temperature, the resulting suspension is added dropwise to stirred ice-water (100 ml). A pale yellow precipitate is filtered off, is washed with water (50 ml), and is recrystallized from $CH_2Cl_2$/n-hexane to give white crystals of rac-threo-(E)-1-Bromo-1-(butan-1',4'-olido)-[3',4':1,2]-6-fluoro-2-methyl-3-(p-methylsulfinylbenzylidene)-indan (0.8 g, 1.9 mmol, 73%). $C_{20}H_{16}BrFO_3S$:435.30; mp. 162° C.

$R_1$=hydrogen, $R_2$=hydrogen, $R_3$=bromo, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfinyl.

EXAMPLE 3 rac-(E)-1-(2'-Buten-1',4'-olido)-[3',4':1,2]-6-fluoro-2-methyl-3-(p-methylsulfonylbenzylidene)-indan A solution of rac-threo-(E)-1-Bromo-1-(butan-1',4'-olido)-[3',4':1,2]-6-fluoro-2-methyl-3-(p-methylsulfonylbenzylidene)-indan from Example 1 (7.3 g, 16.1 mmol) in $CH_2Cl_2$ (50 ml) is treated with N,N-diisopropylethylamine (3.7 ml, 21.3 mmol) for 24 h at room temperature, is extracted with cold aqueous hydrochloric acid (10%, 2×100 ml), and water (3×100 ml). The organic phase is dried ($MgSO_4$), and is evaporated. The residue is purified by flash chromatography ($SiO_2$, $CHCl_3$:Methylisobutylketone 8:2, $R_f$=0.65), to give white crystals of rac-(E)-1-(2'-Buten-1',4'-olido)-[3',4':1,2]-6-fluoro-2-methyl-3-(p-methylsulfonylbenzylidene)-indan (3.9 g, 10.6 mmol, 66%). $C_{20}H_{15}FO_4S$: 370.40; mp. 193° C.

$R_1$=hydrogen, $R_2$ and $R_3$ form a double bond, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl.

EXAMPLE 4 rac-(E)-1-(2'-Buten-1',4'-olido)-[3',4':1,2]-6-fluoro-2-methyl-3-(p-methylsulfinylbenzylidene)-indan A solution of rac-threo-(E)-1-bromo-1-(butan-1',4'-olido)-[3',4':1,2]-6-fluoro-2-methyl-3-(p-methylsulfinylbenzylidene)-indan from Example 2 (0.8 g, 1.9 mmol) in $CH_2Cl_2$ (80 ml) is treated with N,N-diisopropylethylamine (0.6 ml, 3.5 mmol) for 24 h at room temperature, is extracted with cold aqueous hydrochloric acid (10%, 2×10 ml), and water (3×10 ml). The organic phase is dried ($MgSO_4$), and is evaporated. The residue is purified by flash chromatography ($SiO_2$, $CHCl_3$:Methylisobutylketone 8:2), to give white crystals of rac-(E)-1-(2'-Buten-1',4'-olido)-[3',4':1,2]-6-fluoro-2-methyl-3-(p-methylsulfinylbenzylidene)-indan (0.5 g, 1.4 mmol, 74%). $C_{20}H_{15}FO_3S$: 354.40; mp. 84° C.

$R_1$=hydrogen, $R_2$ and $R_3$ form a double bond, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfinyl.

EXAMPLE 5 rac-threo-(E)-1-Chloro-1-(butan-1',4'-olido)-[3',4':1, 2]-6-fluoro-2-methyl-3-(p-methylsulfonylbenzylidene)-indan To a stirred solution of rac-(E)-1-(2'-buten-1',4'-olido)-[3',4':1,2]-6-fluoro-2-methyl-3-(p-methylsulfonylbenzylidene)-indan from Example 3 (1 g, 2.7 mmol) in THF (30 ml) is added hydrochloric acid (10 ml, 37%). After five days at room temperature, the solution is added dropwise with stirring to ice-water (500 ml). A precipitate is filtered off, is washed with water (200 ml), and recrystallized from chlorinated solvents to give white crystals of rac-threo-(E)-1-chloro-1-(butan-1',4'-olido)-[3',4':1,2]-6-fluoro-2-methyl-3-(p-methylsulfonylbenzylidene)-indan (0.67 g, 1.6 mmol, 61%). $C_{20}H_{16}ClFO_4S$: 406.85; mp. 177° C.

$R_1$=hydrogen, $R_2$=hydrogen, $R_3$=chloro, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl.

EXAMPLE 6 rac-threo-(E)-1-Acetoxy-1-(butan-1',4'-olido)-[3', 4':1,2]-6-fluoro-2-methyl-3-(p-methylsulfonylbenzylidene)-indan rac-(E)-1-(2'-Buten-1',4'-olido)-[3',4':1,2]-6-fluoro-2-methyl-3-(p-methylsulfonylbenzylidene)-indan from Example 3 (1 g, 2.7 mmol) and $NH_4Ac$ (5 g, 64.8 mmol) are melted together at 125° C. for two h. Water (100 ml) is added to the cooled mixture. A precipitate is filtered off, and is washed with water (100 ml). By crystalliztion from methanol, it gives white crystals of rac-threo-(E)-1-acetoxy-1-(butan-1',4'-olido)-[3',4':1,2]-6-fluoro-2-methyl-3-(p-methylsulfonylbenzylidene)-indan (0.53 g, 1.23 mmol, 46%). $C_{22}H_{19}FO_6S$: 430.44; mp. 187° C.

$R_1$=hydrogen, $R_2$=hydrogen, $R_3$=acetoxy, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl.

EXAMPLE 7 rac-threo-(E)-1-Azido-1-(butan-1',4'-olido)-[3,'4':1, 2]-6-fluoro-2-methyl-3-(p-methylsulfonylbenzylidene)-indan A solution of rac-(E)-1-(2'-Buten-1',4'-olido)-[3',4':1,2]-6-fluoro-2-methyl-3-(p-methylsulfonylbenzylidene)-indan from Example 3 (1.0 g, 2.7 mmol) in DMF (10 ml) is stirred with $NaN_3$ (0.2 g, 3 mmol) for 80 min at room temperature, diluted with water (30 ml), and acidified at 0° C. (pH=4, 10% HCl). A yellow precipitate is filtered off, is washed with water, and is chromatographed ($SiO_2$, ethylacetate) to give white crystals of rac-theo-(E)-1-azido-1-(butan-1',4'-olido)-[3',4':1,2]-6-fluoro-2-methyl-3-(p-methylsulfinylbenzylidene)-indan (0.2 g, 0.5 mmol, 19%). $C_{20}CH_{16}FN_3O_4S$: 413.42; mp. 137° C.

$R_1$=hydrogen, $R_2$=hydrogen, $R_3$=azido, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl.

EXAMPLE 8 rac-threo-(E)-1-Methoxy-1-(butan-1',4'-olido)-[3', 4':1,2]-6-fluoro-2-methyl-3-(lp-methylsulfonylbenzylidene)-indan A suspension of rac-(E)-1-(2'-buten-1',4'-olido)-[3',4':1,2]-6-fluoro-2-methyl-3-(p-methylsulfonylbenzylidene)-indan from Example 3 (1.0 g, 2.7 mmol) in MeOH (30 ml) is stirred with methanolic 1N NaOCH₃ (3 ml) for 24 h at room temperature. A white solid is filtered off, is washed with $H_2O$ (50 ml), and from MeOH gives white crystals of rac-theo-(E)-1-methoxy-1-(butan-1',4'-olido)-[3',4':1,2]-6-fluoro-2-methyl-3-(p-methylsulfonylbenzylidene)-indan (0.81 g, 2.0 mmol, 75%). $C_{21}H_{19}FO_4S$: 402.43; mp. 196° C.

$R_1$=hydrogen, $R_2$=hydrogen, $R_3$=methoxy, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl.

EXAMPLE 9 rac-(E)-1-(Butan-1',4'-olido)-[3',4':1,2]-6-fluoro-2-methyl-3-(p-methylsulfonylbenzylidene)-indan A stirred solution of rac-threo-(E)-bromo-1-(butan-1',4'-olido)-[3',4':1,2]-6-fluoro-2-methyl-3-(p-methylsulfonylbenzylidene)-indan from Example 1 (1 g, 2.2 mmol) in 5 ml DMF is treated with portions of $NaBH_4$ (5×0.04 g in 4 hr intervals) at room temperature. The solution is then added slowly to 5% stirred aqueous Hcl (100 ml). A white solid is filtered off, is washed with water (200 ml), and from MeOH gives white crystals of rac-(E)-1-(Butan-1',4'-olido)-[3',4':1,2]-6-fluoro-2-methyl-3-(p-methylsulfonylbenzylidene)-indan (0.65 g, 1.7 mmol, 80%). $C_{20}H_{17}FO_4S$: 372.40; mp. 195° C.

$R_1$=hydrogen, $R_2$=hydrogen, $R_3$=hydrogen, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl.

EXAMPLE 10 rac-lyxo-(E)-1-(Butan-1',4'-olido)-2'3'-(Z)-dihydroxy-[3',4':1,2]-6-fluoro-2-methyl-3-(p-methylsulfonylbenzylidene)-indan A solution of rac-(E)-1-(2'-Buten-1',4'-olido)-[3',4':1,2]-6-fluoro-2-methyl-3-(p-methylsulfonylbenzylidene)-indan from Example 3 (1 g, 2.7 mmol) in $CH_2Cl_2$ (20 ml) is treated with 1 ml water and with $OsO_4$ (0.054 mmol, 1.08 ml solution in t-BuOH) and N-methylmorpholine-N-oxide (0.46 ml, 2.73 mmol) under a nitrogen atmosphere. After five h at room temperature, aqueous $Na_2SO_3$ (1.35 g, 10.7 mmol) in 8 ml water is added with stirring. After two h, the reaction mixture is extracted with $CH_2Cl_2$. The organic phase is washed with $H_2O$ (3×50 ml), is dried ($Na_2SO_4$) and is evaporated. The residue gives white crystals of rac-lyxo-(E)-1-(Butan-1',4'-olido)-2',3'-(Z)-dihydroxy-[3',4':1,2]-6-fluoro-2-methyl-3-(p-methylsulfonylbenzylidene)-indan (0.75 g, 1.5 mml, 70%) from MeOH. $C_{20}H_{17}FO_6S$: 403.40; mp. 128° C.

$R_1$=hydrogen, $R_2$=hydroxy, $R_3$=hydroxy, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl.

EXAMPLE 11 rac-threo-(E)-1-Hydroxy-1-(butan-1',4'-olido)-[3', 4':1,2]-6-fluoro-2-methyl-3-(p-methylsulfonylbenzylidene)-indan rac-(E)-1-(2'-Buten-1',4'-olido)-[3',4':1,2]-6-fluoro-2-methyl-3-(p-methylsulfonylbenzylidene)-indan from Example 3 (1 g, 2.7 mmol) in 30 ml $CH_2Cl_2$ is treated with $Bu_4NOH$ ($Bu_4NHSO_4$ 0.34 g, 1 mmol; NaOH 0.4 g, 10 mmol; 10 ml $H_2O$). After five days at room temperature, the aqueous phase is separated, and is acidified at 0° C. (pH 4, citric acid). The reaction mixture is extracted with $CH_2Cl_2$. The organic phase is washed with $H_2O$, is dried ($Na_2SO_4$) and is evaporated. The residue gives white crystals from $CH_2Cl_2$/n-hexane: 0.30 g, 0.8 mmol, 30%.

$R_1$, $R_2$=hydrogen, $R_3$=OH, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl. $C_{20}H_{17}O_5SF$: 388.41. mp. 93° C.

EXAMPLE 12 rac-threo-(E)-1-(N,N'-diethylaminoethanethio)-1-(butan-1',4'-olido)-[3',4':1,2]-6-fluoro-2-methyl-3-(p-methylsulfonylbenzylidene)-indan rac-(E)-1-(2'-Buten-1',4'-olido)-[3',4':1,2]-6-fluoro-2-methyl-3-(p-methylsulfonylbenzylidene)-indan from Example 3 (1 g, 2.7 mmol) in 20 ml DMF/1 ml glacial acetic acid is treated with 2-diethylamioethanethiol•HCl (0.49 g, 2.9 mmol) at room temperature. After 10 days, the reaction mixture is added to 200 g ice. A precipitate is filtered off. The filtrate is neutralized with $NaHCO_3$ (5% in water). A white precipitate is filtered off, is washed with water (200 ml), and is recrystallized from $CH_2Cl_2$/n-hexane to give white crystals: 0.56 g, 1.1 mmol, 41% mp. 69° C.

$R_1$, $R_2$=hydrogen, $R_3$=S—$CH_2CH_2$—$N(Et)_2$, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl. $C_{26}H_{30}FNO_4S_2$: 503.64.

EXAMPLE 13 rac-threo-(E)-1-Cyano-1-(butan-1',4'-olido)-[3',4':1, 2]-6-fluoro-2-methyl-3-(p-methylsulfonylbenzylidene)-indan rac-(E)-1-(2'-Buten-1',4'-olido)-[3',4':1,2]-6-fluoro-2-methyl-3-(p-methylsulfonylbenzylidene)-indan from Example 3 (1 g, 2.7 mmol) in 20 ml DMF is added to a solution of NaCN (0.3 g, 6 mmol) in 30 ml DMF/5 ml glacial acetic acid at room temperature. After 7 days, the reaction mixture is added to 200 g ice. A white precipitate is filtered off, is washed with water (200 ml), and is recrystallized from MeOH to give crystals. 0.84 g, 2.1 mmol, 78% mp. 224° C.

$R_1$, $R_2$=hydrogen, $R_3$=CN, $R_4$=6-fluoro, $R_5$=hydrogen, $R_6$ and $R_8$ form a double bond, $R_7$=methyl, $R_9$=hydrogen, $R_{10}$ and $R_{11}$=hydrogen, and $R_{12}$=methylsulfonyl. $C_{21}H_{16}NO_4SF$: 397.42.

EXAMPLE 14 rac-(E)-1-(2'-Buten-1',4'-olido)-[3',4':1,2]-5,6-difluoro-2-methyl-3-(p-methylsulfinylbenzylidene)-indan (A) 3,4-difluorobenzaldehyde In a 250 ml three-necked flask equipped with a magnetic stirrer, thermometer, condenser, and dropping funnel is placed 25.6 g (0.2 mol) of 3,4-difluorotoluene. The liquid is heated to 105° and illuminated as 67 g (0.42 mol) of bromine is added slowly. The temperature is kept between 105°–110° C. while the first half of the bromine is added over a period of one hour. The rest of the bromine is added over approx. a 2 hour period, and the temperature is raised to 150° and kept there for 5 minutes. The reaction mixture is cooled and transferred to a 1 liter 3-necked flask with a motor driven stirrer and condenser. 120 ml H$_2$O and 90 g of calcium carbonate are added, and the mixture is refluxed for 20 h with good stirring. The reaction mixture is steam distilled until no further oil is collected. The oil is taken up in methylene chloride and dried over MgSO$_4$. Evaporation of the solvent yields 3,4-difluorobenzaldehyde which is used without further purification.

(B) 3,4-difluoro-α-methylcinnamic acid

A mixture of 2.88 g (0.02 mol) of 3,4-difluorobenzaldehyde, 3.24 g (0.025 mol) of propionic anhydride and 0.92 g (0.02 mol) of sodium propionate under nitrogen is heated at 135° C. with magnetic stirrer for 20 h. The reaction mixture is poured onto 50 ml of water. A solid precipitates, which dissolves when 50 ml of saturated K$_2$CO$_3$ is added with stirring. The basic solution is extracted with ether (2×100 ml). The aqueous phase is then poured into an excess of concentrated HCl and ice. The precipitated white solid is filtered and dried to give 3,4-difluoro-α-methylcinnamic acid, m.p. 122°–125° C.

(C) 3,4-difluoro-α-methylhydrocinnamic acid 28 g (0.141 mol) of 3,4-difluoro-α-methylcinnamic acid, 1 g of PtO$_2$ in 250 ml of MeOH is hydrogenated at 45 p.s.i. until the theoretical uptake is completed. The catalyst is filtered off, and the material evaporated to one-third its volume. A 15% potassium hydroxide solution (10 ml) is added, and the mixture refluxed for 30 minutes when it is poured into water and extracted with ether (2×100 ml). The aqueous layer is acidified with concentrated HCl and ice. The oil which comes out is extracted into ether, the ether solution dried over MgSO$_4$ and evaporated to leave a clear oil which crystallizes. 3,4-difluoro-α-methylhydrocinnamic acid, m.p. 55°–56° C., is isolated.

(D) 5,6-difluoro-2-methyl-1-indanone 20 g (0.1 mol) of 3,4-difluoro-α-methylhydrocinnamic acid is added to 250 g of polyphosphoric acid. The mixture is efficiently stirred and heated on a steam bath for 2 h. The mixture is poured onto ice-water (400 ml). The precipitate is extracted with ether (3×100 ml). The extract is washed with saturated potassium carbonate, water and then dried (MgSO$_4$). The ether solution when evaporated leaves solid 5,6-difluoro-2-methyl-1-indanone (m.p. 66°–68° C.) which is used without further purification.

(E) 5,6-difluoro-2-methylindene-3-acetic acid, methyl ester

A mixture of 9.1 g (0.05 mol) of 5,6-difluoro-2-methyl-1-indanone, 4.0 g of "activated" zinc dust, 7.6 g (0.05 mol) of methyl bromoacetate and a crystal of iodine in 250 ml of dry benzene is refluxed for 4–5 h. TLC (20% Et$_2$O 80% pet. ether on Si gel) shows greater than 95% conversion at this time. The reaction mixture is poured onto 250 ml of 5% H$_2$SO$_4$, separated, and dried (MgSO$_4$). Removal of solvent leaves an oily hydroxy ester. The crude ester is redissolved in 100 ml of benzene and phosphorus pentoxide (20 g) is added. The mixture is refluxed for 30 minutes (no stirrer necessary) and decanted. The residue is washed with benzene, the organic layers are combined, are washed with water (2×100 ml) and are dried (MgSO$_4$). The benzene when evaporated leaves 5,6-difluoro-2-methylindene-3-acetic acid, methyl ester, m.p. 86°–90° C.

(F) 5,6-difluoro-2-methyl-1-(p-methylthiobenzylidene)-indene-3-acetic acid)

1.19 g (5.0 mmol) of 5,6-difluoro-2-methylindene-3-acetic acid methyl ester is dissolved in 10 ml of dry pyridine followed by 0.76 g (5.0 mmol) of p-methylthiobenzaldehyde. The flask is placed under nitrogen, and 5.0 g (5.1 mmol) of Triton B is added. The deeply colored solution is allowed to stand overnight, and then 2 ml of water is added. After standing for 15 minutes, it is poured into an excess of water. The organics are extracted with ether (2×50 ml). The aqueous phase is added to 10% HCl-ice. The orange gummy solid which precipitates is extracted into methylene chloride and dried (MgSO$_4$). The solvent is removed to leave an orange solid. The solid is filtered to give a crude product which is recrystallized from benzene to give 5,6-difluoro-2-methyl-1-(p-methylthiobenzylidene)-indene-3-acetic acid. m.p. 181°–182.5° C.

(G) (Z)-5,6-difluoro-2-methyl-1-(p-methylsulfinylbenzylidene)-indene-3-acetic acid To a solution of 0.358 g (1.0 mmol) of 5,6-difluoro-2-methyl-1-(p-methylthiobenzylidene)-indene-3-acetic acid in acetone (10 ml) is added 10–15 ml MeOH. With magnetic stirring 0.32 g (1.5 mmol) of sodium meta periodate is added in 5 ml of water. The proportions of acetone, methanol and water are adjusted if necessary in order to preserve homogeneity. After several minutes, a precipitation of sodium iodate appears. The suspension is stirred at room temperature for 16 h, and is then poured into approximately 50 ml of water and 100 ml methylene chloride. The two phases are separated and extracted twice with methylene chloride. The organic layer is washed with water and dried (MgSO$_4$). The residue after evaporation is dissolved in the minimum amount of boiling ethyl acetate and is allowed to stand for 12 h in the freezer compartment. The deep orange crystals are filtered. The filtrate is reduced to ½ volume and allowed to stand in the cold for several hours to give a large second crop. In this way, 5,6-difluoro-2-methyl-1-(p-methylsulfinylbenzylidene)-3-indenylacetic acid is isolated, m.p. 200°–210° C.

(H) rac-(E)-1-(2'-Buten-1',4'-olido)-[3',4':1,2]-5,6-difluoro-2-methyl-3-(p-methylsulfinylbenzylidene)-indan rac-(E)-1-(2'-Buten-1',4'-olido)-[3',4':1,2]-5,6-difluoro-2-methyl-3-(p-methylsulfinylbenzylidene)-indan is obtained, if (Z)-5,6-difluoro-2-methyl-1-(p-methylsulfinylbenzylidene)-3-indenylacetic acid is reacted according to the procedures of Example 2 and Example 4. C$_{20}$OH$_{14}$F$_2$O$_3$S:372.38.

R$_1$=hydrogen, R$_2$ and R$_3$ form a double bond, R$_4$=6-fluoro, R$_5$=5-fluoro, R$_6$ and R$_8$ form a double bond, R$_7$=methyl, R$_9$=hydrogen, and R$_{12}$=methylsulfinyl.

EXAMPLE 15 rac-(E)-1-(2'-Buten-1',4'-olido)[3',4':1,2]-5,6-difluoro-2-methyl-3-(p-methylsulfonylbenzylidene)-indan (A) (Z)-5,6-difluoro-2-methyl-1-(p-methylsulfonylbenzylidene)-indene-3-acetic acid To (Z)-5,6-difluoro-2-methyl-1-(p-methylsulfinylbenzylidene)-indene-3-acetic acid (0.005 mol) in acetone (15 ml) is added, slowly with stirring, m-chloroperbenzoic acid (0.005 mol). The mixture is heated and evaporated to near dryness at 40° C. The solid is leached with boiling water (4×50 ml) and dried yielding 5,6-difluoro-2-methyl-1-(p-methylsulfonylbenzylindene)-indene-3-acetic acid, m.p. 228°–230° C.

(B) rac-(E)-1-(2'-Buten-1',4'-olido)-[3',4':1,2]-5,6-difluoro-2-methyl-3-(p-methylsulfonylbenzylidene)-indan rac-(E)-1-(2'-Buten-1',4'-olido)-[3',4':1,2]-5,6-difluoro-2-methyl-3-(p-methylsulfonylbenzylidene)-indan is obtained, if (Z)-5,6-difluoro-2-methyl-1-(p-methylsulfonylbenzylidene)-3-indenylacetic acid is reacted according to the procedure of Example 1 and Example 3.

$R_1$=hydrogen, $R_2$ and $R_3$ form a double bond, $R_4$=6-fluoro, $R_5$=5-fluoro, $R_6$ and $R_8$ form a double bond, $R_7$=methyl, $R_9$=hydrogen, and $R_{12}$=methylsulfonyl.

EXAMPLE 16 rac-(E)-1-(2'-Buten-1',4'-olido)-[3',4':1,2]-6-dimethylamino-2-methyl-3-(p-methylsulfinylbenzylidene)-indan (A) Methyl 3-hydroxy-2-methyl-5-nitro-3-indenylacetate A solution of 13.4 g of 2-methyl-6-nitroindanone and 19.3 g of methyl bromoacetate in 45 ml benzene is added over a period of 5 minutes to 21 g of zinc amalgam (prepared according to Org. Syn. Coll., Vol. 3) in 110 ml benzene and 40 ml dry ether. A few crystals of iodine are added to start the reaction, and the reaction mixture is maintained at reflux temperature (ca. 650) with external heating. At three-hour intervals, two batches of 10 g zinc amalgam and 10 g bromoester are added, and the mixture is then refluxed for 8 h. After addition of 30 ml of ethanol and 150 ml of acetic acid, the mixture is poured into 700 ml of 1:1 aqueous acetic acid. The organic layer is separated, and the aqueous layer is extracted twice with ether. The combined organic layers are washed thoroughly with water, ammonium hydroxide and water. The hydroxy ester product is dried over sodium sulfate. Evaporation of solvent in vacuo is followed by pumping at 80° (bath temp.) (1–2 mm).

A mixture of the above crude hydroxyester, 20 g of p-toluenesulfonic acid monohydrate and 20 g of anhydrous calcium chloride in 250 ml toluene is refluxed overnight. The solution is filtered, and the solid residue is washed with benzene. The combined benzene solution is washed with water, sodium bicarbonate, water and is then dried over sodium sulfate. After the mixture is condensed, 30 ml of ethanol and 50 ml of acetic acid are added. The mixture is then poured into 700 ml of water. Extraction with ether gives methyl 3-hydroxy-2-methyl-5-nitro-3-indenylacetate.

(B) Methyl 5-dimethylamino-2-methyl-3-indenylacetate

A solution of 0.05 mol of methyl 3-hydroxy-2-methyl-5-nitro-3-indenylacetate, 0.2 mol of 38% aqueous formaldehyde and 2 ml of acetic acid in 100 ml ethanol is reduced catalytically in the presence of a 10% Pd/C catalyst under 40 lb. p.s.i. hydrogen pressure at room temperature. The solution is filtered, evaporated and chromatographed on 300 g of silica gel to give methyl 5-methylamino-3-hydroxy-2-methyl-3-indenylacetate. The hydroxy ester is then dehydrated to methyl 5-dimethylamino-2-methyl-3-indenylacetate.

(C) 1-p-methylthiobenzylidene-5-dimethylamino-2-methyl-3-indenyl acetic acid

To a solution of 2.5 g of the ester from Part B of this example in 15 ml of 1,2-dimethoxyethane at 0° is added 1.5 g of p-methylthiobenzaldehyde followed by 1.1 g of potassium t-butoxide. The reaction mixture is kept in the ice-bath for 4 h and is then allowed to stand at room temperature for 18 h. The mixture is diluted with 15 ml of ether and the potassium salt is filtered. The salt is dissolved in 30 ml of water and neutralized with dilute hydrochloric acid to pH 6–6.5. The crude acid precipitated is collected by filtration and chromatographed on a silica gel column, using ether-petroleum ether (v./v. 50–100%) as eluent to give pure 1-p-methylthiobenzylidene-5-dimethylamino-2-methyl-3-indenylacetic acid which may be oxidized to 1-p-methylsulfinylbenzylidene-5-dimethylamino-2-methyl-3-indenylacetic acid and 1-p-methylsulfonylbenzylidene-5-dimethylamino-2-methyl-3-indenylacetic acid as described above (Example 1).

(D) rac-(E)-1-(2'-buten-1',4'-olido)-[3',4':1,2]-6-dimethylamino-2-methyl-3-(p-methylsulfinylbenzylidene)-indan rac-(E)-1-(2'-Buten-1',4'-olido)-[3',4':1,2]-6-dimethylamino-2-methyl-3-(p-methylsulfinylbenzylidene)-indan is obtained, if (Z)-5-dimethylamino-2-methyl-1-(p-methylsulfinylbenzylidene)-3-indenylacetic acid from part (C) is reacted according to the procedure of Example 2 and Example 4. $C_{22}H_2INO_3S$:379.47.

$R_1$=hydrogen, $R_2$ and $R_3$ form a double bond, $R_4$=6-dimethylamino, $R_3$=hydrogen, $R_6$ and $R_8$ form a double bond, $R_7$=methyl, $R_9$=hydrogen, and $R_{12=}$methylsulfinyl.

EXAMPLE 17 rac-(E)-1-(2'-Buten-1',4'-olido)-[3',4':1,2]-6-dimethylamino-2-methyl-3-(p-methylsulfonylbenzylidene)-indan rac-(E)-1-(2'-Buten-1',4'-olido)-[3',4':1,2]-6-dimethylamino-2-methyl-3-(p-methylsulfonylbenzylidene)-indan is obtained, if (Z)-5-dimethylamino-2-methyl-1-(p-methylsulfonylbenzylidene)-3-indenylacetic acid from Example 16C is reacted according to the procedure of Example 1 and Example 3. $C_{22}H_{21}NO_4S$:395.47.

$R_1$=hydrogen, $R_2$ and $R_3$ form a double bond, $R_4$=6-dimethylamino, $R_5$=hydrogen, $R_6$ and $R_8$ form a double bond, $R_7$=methyl, R=hydrogen, and $R_{12=}$methylsulfonyl.

EXAMPLE 18 rac-(E)-1-(2'-Buten-1',4'-olido)[3',4':1,2]-6-methoxy-2-methyl-3-(p-methylsulfinylbenzylidene)-indan (A) α-Methyl-β-(p-methoxyphenyl)propionic acid To a solution of 2.3 g (0.1 mol) of sodium in 100 ml of absolute alcohol is added 17.4 g (0.1 mol) of diethyl methylmalonate and 17.3 g (0.1 mol) of p-methoxybenzylchloride. The mixture is heated under reflux in a water bath for 3 h. The reaction mixture is poured into water, and the aqueous solution is extracted six times with ether and dried. It is then evaporated to yield diethyl methyl-p-methylthiobenzyl malonate. The crude product is then saponified by heating with excess 4% sodium hydroxide in aqueous ethanolic solution. The solution thus formed is concentrated, extracted with ether to remove any neutral material, and acidified with dilute sulfuric acid. The acidic mixture is heated on a steam bath for one hour, cooled and then extracted with ether. Evaporation of the ether solution gives α-methyl-β-(p-methoxyphenyl)propionic acid.

(B) 6-methoxy-2-methylindanone

α-Methyl-β-(p-methoxyphenyl)propionic acid (15 g) is added to 170 g of polyphosphoric acid at 50° and the mixture is heated at 83°–90° for 2 h. The syrup is poured into iced water, stirred for one-half hour and then extracted with ether three times. The ether solution is washed with water twice and 5% NaHCO$_3$ five times until all the acidic material has been removed. The remaining neutral solution is washed with water and dried over sodium sulfate. Evaporation of the solution gives the indanone as a pale yellow oil.

(C) Methyl 5-methoxy-2-methyl-3-indenylacetate

A solution of 13.4 g of 6-methoxy-2-methylindanone and 19.3 g of methyl bromoacetate in 45 ml benzene is added over a period of 5 minutes to 21 g of zinc amalgam (prepared according to Org. Syn. Coll., Vol. 3) in 110 ml benzene and 40 ml dry ether. A few crystals of iodine are added to start the reaction, and the reaction mixture is maintained at reflux temperature (ca. 65°) with external heating. At three-hour intervals two batches of 10 g zinc amalgam and 10 g bromoester are added, and the mixture is then refluxed for 8 h. After addition of 30 ml of ethanol and 150 ml of acetic acid, the mixture is poured into 700 ml of 1:1 aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temp.) (1–2 mm) gives crude methyl (1-hydroxy-2-methyl-6-methoxy-indanyl)acetate.

A mixture of the above crude hydroxyester, 20 g of p-toluenesulfonic acid monohydrate and 20 g of anhydrous calcium chloride in 250 ml toluene is refluxed overnight. The solution is filtered and the solid residue is washed with benzene. The combined benzene solution is washed with water, sodium bicarbonate, water and is then dried over sodium sulfate. After evaporation, the crude methyl 5-methoxy-2-methyl-3-indenylacetate is chromatographed on acid-washed alumina, and the product is eluted with petroleum ether-ether (v./v. 50–100%).

(D) 5-methoxy-2-methyl-1-(p-methylthiobenzylidene)-3-indenylacetic acid

To a solution of methyl 5-methoxy-2-methyl-3-indenylacetate 8.7 g (0.037 mol) and p-methylthiobenzaldehyde, 6.3 g (1.1. equivalent) is added 16 ml (2.0 equivalents) of 25% methanolic sodium methoxide. The mixture is stirred at reflux under nitrogen for 2 h. An equal volume of water is added dropwise and refluxing is continued for 30 min. The solution is cooled, is diluted with water and is extracted with ether. Residual ether is blown off with nitrogen. The aqueous solution is acidified with 50% glacial acetic acid. The precipitated product is collected and is washed thoroughly with water. The crude product is crystallized from methanol to give pure 5-methoxy-2-methyl-1-(p-methylthiobenzylidene)-3-indenylacetic acid (m.p. 195°–196°).

(E) 5-methoxy-2-methyl-1-(p-methylsulfinylbenzylidene)-3-indenylacetic acid

A solution of sodium periodate (0.214 g) (0.001 mol) in 3 ml of water is added dropwise to 5-methoxy-2-methyl-1-(p-methylthiobenzyidene)-3-indenylacetic acid (0.352 g) (0.001 mol) in 25 ml methanol and enough acetone to cause solution. This solution is stirred overnight at room temperature and is filtered. The filtrate is evaporated at 30° to a small volume which causes the product to precipitate. The suspension is diluted with several volumes of water and is cooled. The collected product is dried in vacuo over potassium hydroxide pellets and then in a vacuum oven at 70° to give 5-methoxy-2-methyl-1-(p-methylsulfinylbenzylidene)-3-indenylacetic acid (m.p. 200.5°–203.5°).

5-methoxy-2-methyl-1-(p-methylsulfonylbenzylidene)-3-indenylacetic acid is prepared by the addition of 1.0 mol of m-chloroperbenzoic acid per mol of 5-methoxy-2-methyl-1-(p-methylsulfinylbenzylidene)-3-indenylacetic acid in an acetone solution.

(F) rac-(E)-1-(2'-Buten-1',4'-olido)-[3',4':1,2]-6-methoxy-2-methyl-3-(p-methylsulfinylbenzylidene)-indan rac-(E)-1-(2'-Buten-1',4'-olido)-[3',4':1,2]-6-methoxy-2-methyl-3-(p-methylsulfinylbenzylidene)-indan is obtained, if (Z)-5-methoxy-2-methyl-1-(p-methylsulfinylbenzylidene)-3-indenylacetic acid is reacted according to the procedure of Example 2 and Example 4. C$_{21}$H$_{18}$O$_4$S:366.43.

R$_1$=hydrogen, R$_2$ and R$_3$ form a double bond, R$_4$=6-methoxy, R$_5$=hydrogen, R$_6$ and R$_8$ form a double bond, R$_7$=methyl, R$_9$=hydrogen, R$_{10}$ and R$_{11}$=hydrogen, and R$_{12}$=methylsulfinyl.

EXAMPLE 19 rac-(E)-1-(2'-Buten-1',4'-olido)-[3',4':1,2]-6-methoxy-2-methyl-3-(p-methylsulfonylbenzylidene)-indan rac-(E)-1-(2'-Buten-1',4'-olido)-[3',4':1,2]-6-methoxy-2-methyl-3-(p-methylsulfonylbenzylidene)-indan is obtained, if (Z)-5-methoxy-2-methyl-1-(p-methylsulfonylbenzylidene)-3-indenylacetic acid from Example 18 part (E) is reacted according to the procedure of Example 1 and Example 3. C$_{21}$H$_{18}$O$_5$S:382.43.

R$_1$=hydrogen, R$_2$ and R$_3$ form a double bond, R=6-methoxy, R$_5$=hydrogen, R$_6$ and R$_8$ form a double bond, R$_7$=methyl, R$_9$=hydrogen, R$_{10}$ and R$_{11}$=hydrogen, and R$_{12}$=methylsulfonyl.

EXAMPLE 20 rac-(E)-1-(2'-Buten-1',4'-olido)-[3',4':1,2]-5-fluoro-6-methoxy-2-methyl-3-(p-methylsulfinylbenzylidene)-indan (A) 3-fluoro-4-methoxybenzaldehyde To a solution of o-fluoroanisole, 101 g (0.80 mol) in 50 ml dry methylene chloride is added dropwise over 30 minute a solution of titanium tetrachloride, 182 g (0.96 mol, 1.2 equiv.) and α,α-dichloromethylmethyl ether, 110 g (0.96 mol) in an equal volume of methylene chloride. The temperature is maintained at 10°–20° C. with an ice-bath. The mixture is stirred at room temperature for one hour longer, and then poured over crushed ice-water with stirring. Ether (1 l) is added, and the mixture is stirred under nitrogen until solution occurs. The organic layer is extracted with water, sodium bicarbonate solution and is dried (MgSO$_4$). The solvent is evaporated at 30° to leave crude product as an oil. When vacuum distilled through a jacketed Vigreux column, the oil gives 3-fluoro-4-methoxybenzaldehyde, B.P. 120°–121° C. at 10 mm. Hg; $R_f$ 0.6 on a silica-gel G plate with methylene chloride.

(B) 3-fluoro-4-methoxy-α-methylcinnamic acid

A mixture of 3-fluoro-4-methoxybenzaldehyde, 34.2 g (0.22 mol), propionic anhydride, 50 g (0.38 mol) and sodium propionate, 21 g (0.22 mol), is stirred under nitrogen at 150° C. for 15 h. The reaction mixture is then poured into 1.3 l of water with stirring and the product precipitated. 2.0N potassium hydroxide solution (500 ml) is added, and the mixture is stirred for several hours, until the acid has dissolved.

The aqueous solution is extracted with ether and then acidified with concentrated hydrochloric acid with stirring. The precipitated product is collected, washed thoroughly with water and dried in a vacuum oven at 50° C. over potassium hydroxide pellets to give 3-fluoro-α-methyl-4-methoxycinnamic acid, m.p. 167°–169° C.; $R_f$ 0.5 on silica-gel G with methylene chloride-methanol (1:1).

(C) 3-fluoro-4-methoxy-α-methyl dihydrocinnamic acid 3-fluoro-4-methoxy-α-methylcinnamic acid, 49.5 g (0.236 mol) in 800 ml methanol is hydrogenated at 43 lbs. pressure and room temperature until the theoretical uptake of hydrogen has occurred (24 min. at 20° C., using 1.5 g platinum oxide catalyst). The solution is filtered and is evaporated with warming to 60° to give 3-fluoro-4-methoxy-α-methyl dihydrocinnamic acid, $R_f$ 0.5 on silica-gel G with methylene chloride-methanol (9:1).

(D) 5-fluoro-6-methoxy-2-methylindanone

A mixture of 3-fluoro-α-methyl-4-methoxy dihydrocinnamic acid, 49.3 g (0.23 mol) in 500 g of polyphosphoric acid is heated at 950 C. on a steam bath with occasional agitation for 75 min. The dark red solution is poured into 3.0 l of water, and the mixture is stirred overnight. The precipitated product is collected, is washed thoroughly with water, and is taken up in ether. The ether solution is extracted with aqueous potassium bicarbonate (4×), diluted with methylene chloride and dried (MgSO$_4$).

The organic solution is evaporated and recrystallized from methylene chloride petroleum ether to give 5-fluoro-6-methoxy-2-methylindanone, (m.p. 76°–78°).

(E) Methyl 6-fluoro-5-methoxy-2-methyl-3-indenyl-acetate

Into a 500 ml three-necked flask fitted with mechanical stirrer, reflux condenser, drying tube, dropping funnel and nitrogen inlet is placed 6.0 g zinc sheet and 100 ml of dry benzene. A few milliliters of a solution of 21.3 g (0.11 mol) of 5-fluoro-6-methoxy-2-methylindanone and 18.36 g (0.121 mol) of methyl bromoacetate in 100 ml of dry benzene is added at a time. A crystal of iodine is added. The mixture is gently heated with stirring. After the iodine color has disappeared, the remainder of the mixture is added gradually. The mixture is heated at reflux temperature for 18 h, and is then poured onto 600 ml of 5% H$_2$SO$_4$ water and about 500 g of ice. Some ether is added. The organic layer is separated and is washed with three portions of 5% H$_2$SO$_4$, KHCO$_3$ solution and finally water. The organic layer is dried (MgSO$_4$) and is concentrated to give 27.6 g of reddish oil which crystallizes slowly. Thin-layer chromatography on silica-gel G with methylene chloride methanol (99:1) shows product at $R_f$ 0.5.

Without further purification, the hydroxy ester is dehydrated to the indenylacetate. In 200 ml of dry benzene, 14.2 g (53 mol) of crude ester and 36 g of phosphorus pentoxide are refluxed with stirring for ½ hour. After cooling, the reaction mixture is filtered. The solid residue is triturated with benzene. The benzene filtrate is washed with two portions of salt water, is dried (MgSO$_4$), and is concentrated, to give a slightly colored oil which rapidly crystallizes. The crude product is recrystallized from methylene chloride-petroleum ether to give methyl-6-fluoro-5-methoxy-2-methyl-3-indenyl-acetate (m.p. 61°–62°).

(F) 6-fluoro-5-methoxy-2-methyl-1-(p-methylthiobenzylidene)-3-indenylacetic acid To a solution of methyl-6-fluoro-5-methoxy-2-methyl-3-indenyl acetate, 9.3 g (0.037 mol) and p-methylthiobenzaldehyde, 6.3 g (1.1 equivalent) is added 16 ml (2.0 equivalents) of 25% methanolic sodium methoxide. The mixture is stirred at reflux under nitrogen for 2 h. An equal volume of water is added dropwise and refluxing continues for 30 minutes. The solution is cooked, diluted with water and extracted with ether. Residual ether is blown off with nitrogen. The aqueous solution is acidified with 50% glacial acetic acid. The precipitated product is collected and washed thoroughly with water. The crude produced is recrystallized from methanol to give 6-fluoro-5-methoxy-2-methyl-1-(p-methylthiobenzylidene)-2-indenylacetic acid, m.p. 172°–174°.

(G) 6-fluoro-5-methoxy-2-methyl-1-(p-methylsulfinyl-benzylidene)-3-indenylacetic acid A solution of sodium periodate, 4.28 g (20 mol) in 40 ml of water is added dropwise to 6-fluoro-5-methoxy-2-methyl-1-(p-methylthiobenzylidene)-3-indenylacetic acid, 3.70 g (10 mmol) in 300 ml methanol and enough acetone to cause solution. This solution is stirred overnight at room temperature and filtered. The filtrate is evaporated at 30° to a small volume which causes the product to precipitate. The suspension is diluted with several volumes of water, and is cooled. Collected crystals are washed with water and methanol-water (1:1). The product is dried in vacuo over potassium hydroxide pellets and then in a vacuum oven at 70° C. The crude product is recrystallized from methylene chloride-petroleum ether to give 6-fluoro-5-methoxy-2-methyl-1-(p-methylsulfinyl-benzylidene)-3-indenylacetic acid (m.p. 190°–193°). 6-fluoro-5-methoxy-2-methyl-1-(p-methylsulfonylbenzylidene)-3-indenylacetic acid is prepared according to the procedure of Example 1, part G by the addition of 1.0 mol of m-chloroperbenzoic acid per mol of 6-fluoro-5-methoxy-2-methyl-1-(p-methylsulfinylbenzylidene)-3-indenyl acetic acid in an acetone solution.

(H) rac-(E)-1-(2'-Buten-1',4'-olido)-[3',4':1,2]-5-fluoro-6-methoxy-2-methyl-3-(p-methylsulfinylbenzylidene)-indan rac-(E)-1-(2'-Buten-1', 4'-olido)-[3',4':1,2]-5-fluoro-6-methoxy-2-methyl-3-(p-methylsulfinylbenzylidene)-indan is obtained, if (Z)-5-methoxy-6-fluoro-2-methyl-1-(p-methylsulfinylbenzylidene)-3-indenylacetic acid from part (G) is reacted according to the procedure of Example 2 and Example 4. $C_{21}H_{17}FO_4S$:384.42.

$R_1$=hydrogen, $R_2$ and $R_3$ form a double bond, $R_4$=6-methoxy, $R_5$=5-fluoro, $R_6$ and $R_8$ form a double bond, $R_7$=methyl, $R_9$=hydrogen, and $R_{12}$=methylsulfinyl.

EXAMPLE 21 rac-(E)-1-(2'-Buten-1', 4'-olido)-[3',4':1,2]-5-fluoro-6-methoxy-2-methyl-3-(p-methylsulfonylbenzylidene)-indan rac-(E)-1-(2'-Buten-1',4'-olido)-[3',4':1,2]-5-fluoro-6-methoxy-2-methyl-3-(p-methysulfonylbenzylidene)-indan is obtained, if (Z)-5-methoxy-6-fluoro-2-methyl-1-(p-methylsulfonylbenzylidene)-3-indenylacetic acid from Example 20 part (G) is reacted according to the Example 1 and Example 3. $C_{21}H_{17}FO_5S$:400.42

$R_1$=hydrogen, $R_2$ and $R_3$ form a double bond, $R_4$=6-methoxy, $R_5$=5-fluoro, $R_6$ and $R_8$ form a double bond, $R_7$=methyl, $R_9$=hydrogen, and $R_{12}$=methylsulfonyl.

EXAMPLE 22 rac-(E)-1-(2'-Buten-1',4'-olido)-|3',4':1,2|-6-hydroxy-2-methyl-3-(p-methysulfinylbenzylidene)-indan (A) 5-hydroxy-2-methyl-1-(p-methylthiobenzylidene)-3-indenyl acetic acid The reaction of Example 18D is repeated except that the starting materials are methyl 5-hydroxy-2-methyl-3-indenylacetate and p-methylthiobenzaldehyde. Using the same reaction conditions and techniques, 5-hydroxy-2-methyl-1-(p-methyithiobenzylidene)-3-indenyl acetic acid is obtained.

(B) 5-hydroxy-2-methyl-1-(p-methylsulfinylbenzylidene)-3-indenyl acetic acid

Using the procedure of Example 1, part F, 5-hydroxy-2-methyl-1-(p-methylsulfinylbenzylidene)-3-indenyl acetic acid obtained in part (A).

(C) rac-(E)-1-(2'-buten-1',4'-olido)-|3',4':1,2|-6-hydroxy-2-methyl-3-(p-methylsulfinylbenzylidene)-indan rac-(E)-1-(2'-Buten-1',4'-olido)-|3',4':1,2|-6-hydroxy-2-methyl-3-(p-methylsulfinylbenzylidene)-indan is obtained, if 5-hydroxy-2-methyl-1-(p-methylsulfinylbenzylidene)-3-indenylacetic acid is reacted according to the procedure of Example 2 and Example 4. $C_{20}H_{16}O_4S$:352.40.

$R_1$ hydrogen, $R_2$ and $R_3$ form a double bond, $R_4$=6-hydroxy, $R_5$=hydrogen, $R_6$ and $R_8$ form a double bond, $R_7$=methyl, $R_9$=hydrogen, and $R_{12}$ =methylsulfinyl.

EXAMPLE 23 rac-(E)-1-(2'-Buten-1',4'-olido)-[3',4':1,2|-6-hydroxy-2-methyl-3-(p-methylsulfonylbenzylidene)-indan (A) 5-hydroxy-2-methyl-1-(p-methylsulfonylbenzylidene)-3-indenylacetic acid.

5-hydroxy-2-methyl-1-(p-methylsulfonylbenzylidene)-3-indenylacetic acid is obtained from 5-hydroxy-2-methyl-1-(p-methylsulfinylbenzylidene)-3-indenylacetic acid (see Example 22, part B) using the procedure of Example 1, part H.

(B) rac-(E)-1-(2'-buten-1',4'-olido)-|3',4':1,2|-6-hydroxy-2-methyl-3-(p-methylsulfinylbenzylidene)-indan rac-(E)-1-(2'-Buten-1',4'-olido)-[3',4':1,2|-6-hydroxy-2-methyl-3-(p-methylsulfonylbenzylidene)-indan is obtained, if the (Z)-5-hydroxy-2-methyl-1-(p-methylsulfonylbenzylidene)-3-indenylacetic acid is reacted according to the procedure of Example 1 and Example 3. $C_{20}H_{16}O_5S$:368.40.

$R_1$ =hydrogen, $R_2$ and $R_3$ form a double bond, $R_4$ =6-hydroxy, $R_5$=hydrogen, $R_6$ and $R_8$ form a double bond, $R_7$=methyl, $R_9$=hydrogen, and $R_{12}$=methylsulfonyl.

EXAMPLE 24 rac-(E)-1-(2'-Buten-1',4'-olido)-|3',4':1,2|-6-methoxy-2-methyl-3-benzylidene-indan (A) 5-methoxy-2-methyl-1-benzylidene-3-indenylacetic acid.

5-methoxy-2-methyl-1-benzylidene-3-indenylacetic acid is obtained, if methyl-5-methoxy-2-methyl-3-indenylacetate (see Example 18, part C) is allowed to react with benzaldehyde according to the procedure of Example 18, part D.

(B) rac-(E)-1-(2'-buten-1',4'-olido)-|3',4':1,2|-6-methoxy-2-methyl-3-benzylidene-indan If 5-methoxy-2-methyl-1-benzylidene-3-indenylacetic acid is allowed to react according to the procedure of Example 1 and Example 3, rac-(E)-1-(2'-Buten-1',4'-olido)-|3',4':1,2|-6-methoxy-2-methyl-3-benzylidene-indan is obtained. $C_{20}H_{16}O_3$ mw. 304.34

$R_1$=hydrogen, $R_2$ and $R_3$ form a double bond, $R_4$=6-methoxy, $R_5$=hydrogen, $R_6$ and $R_8$ form a double bond, $R_7$=methyl, $R_9$=hydrogen, $R_{10}$ and $R_1$=hydrogen, and $R_{12}$= hydrogen.

EXAMPLE 25 rac-(E)-1-(2'-Buten-1',4'-olido)-[3',4':1,2|-6-methoxy-2-methyl-3-(p-chlorobenzylidene)-indan (A) 5-methoxy-2-methyl-1-(p-chlorobenzylidene)-3-indenylacetic acid 5-methoxy-2-methyl-1-(p-chlorobenzylidene)-3-indenylacetic acid is obtained, if methyl-5-methoxy-2-methyl-3-indenylacetate (see Example 18, part C) is reacted with p-chlorobenzaldehyde according to the procedure of Example 18, part D.

(B) rac-(E)-1-(2'-Buten-1',4'-olido)-[3',4':1,2|-6-methoxy-2-methyl-3-(p-chlorobenzylidene)-indan If 5-methoxy-2-methyl-1-(p-chlorobenzylidene)-3-indenylacetic acid is reacted according to the procedure of Example 1 and Example 3, rac-(E)-1-(2'-Buten-1',4'-olido)-[3',4':1,2|-6-methoxy-2-methyl-3-(p-chlorobenzylidene)-indan is obtained. $C_{20}H_{15}ClO_3$ mw. 338.79

$R_1$=hydrogen, $R_2$ and $R_3$ form a double bond, $R_4$=6-methoxy, $R_5$=hydrogen, $R_6$ and $R_8$ form a double bond, $R_7$=methyl, $R_9$=hydrogen, $R_{10}$ and $R_1$=hydrogen, and $R_{12}$= chloro.

EXAMPLE 26 rac-(E)-1-(2'-Buten-1',4'-olido)[3',4':1,2|-6-methoxy-2-methyl-3-(p-methylbenzylidene)-indan (A) 5-methoxy-2-methyl-1-(p-methylbenzylidene)-3-indenylacetic acid 5-methoxy-2-methyl-1-(p-methylbenzylidene)-3-indenylacetic acid is obtained, if methyl-5-methoxy-2-methyl-3-indenylacetate (see Example 18, part C) is reacted with p-toluylaldehyde according to the procedure of Example 18, part D.

(B) rac-(E)-1-(2'-Buten-1',4'-olido)-|3',4':1,2|-6-methoxy-2-methyl-3-(p-methylbenzylidene)-indan If 5-methoxy-2-methyl-1-(p-methylbenzylidene)-3-indenylacetic acid is reacted according to the procedure of Example 1 and Example 3, rac-(E)-1-(2'-Buten-1',4'-olido)-[3',4':1,2]-6-methoxy-2-methyl-3-(p-methylbenzylidene)-indan is obtained. $C_{21}H_{18}O_3$ mw. 318.37

$R_1$=hydrogen, $R_2$ and $R_3$ form a double bond, $R_4$=6-methoxy, $R_5$=hydrogen, $R_6$ and $R_8$ form a double bond, $R_7$=methyl, $R_9$=hydrogen, $R_{10}$ and $R_{11}$=hydrogen, and $R_{12}$=methyl.

EXAMPLE 27 rac-(E)-1-(2'-buten-1',4'-olido)-[3',4':1,2]-6-fluoro-2-methyl-3-benzylidene-indan (A) (Z)-5-Fluoro-2-methyl-1-benzylidene-3-acetic acid When 5-Fluoro-2-methylindene-3-acetic acid (see Example 1, part D) is allowed to react with benzaldehyde according to the procedure of Example 1 (part E), (Z)-5-Fluoro-2-methyl-1-benzylidene-3-acetic acid is obtained. $C_{19}H_{15}FO_2$:294.32; mp. 184 ° C.

(B) rac-(E)-1-(2'-buten-1l',4'-olido)-[3',4':1,2]-6-fluoro-2-methyl-3-benzylidene-indan When (Z)-5-Fluoro-2-methyl-1-benzylidene-3-acetic acid is allowed to react according to the procedures of Example 2 and Example 4, one obtains rac-(E)-1-(2'-buten-1',4'-olido)-[3',4':1,2]-6-fluoro-2-methyl-3-benzylidene-indan. $C_{19}H_{13}FO_2$:292.30; mp. 111° C.

$R_1$=hydrogen, $R_2$ and $R_3$ form a double bond, $R_4$6-fluoro, $R_5$=hydrogen, $R_6$ and $R_8$ form a double bond, $R_7$=methyl, $R_9$, $R_{10}$, $R_{11}$, and $R_{12}$=hydrogen.

EXAMPLE 28 rac-(E)-1-(2 '-buten-1',4'-olido)-[3',4':1,2]-6-fluoro-2-methyl-3-(3,4,5-trimethoxybenzylidene)-indan (A) (Z)-5-Fluoro-2-methyl-1-(3,4,5-trimethoxybenzylidene)-3-acetic acid When 5-Fluoro-2-methylindene-3-acetic acid (see Example 1, part D) is allowed to react with 3,4,5-trimethoxybenzaldehyde according to the procedure of Example 1 (part E), one obtains (Z)-5-Fluoro-2-methyl-1-(3,4,5-trimethoxybenzylidene)-3-acetic acid. $C_{22}H_{21}FO_5$:384.40; mp. 168 ° C.

(B) rac-(E)-1-(2'-buten-1',4'-olido)-[3',4':1,2]-6-fluoro-2-methyl-3-(3,4,5-trimethoxybenzylidene)-indan When (Z)-5-Fluoro-2-methyl-1-(3,4,5-trimethoxybenzylidene)-3-acetic acid is allowed to react according to the procedures of Example 2 and Example 4, one obtains rac-(E)-1-(2'-buten-1',4'-olido)-[3',4':1,2]-6-fluoro-2-methyl-3-(3 ,4,5-trimethoxybenzylidene)-indan. $C_{22}H_{19}FO_5$:382.38; mp. 150° C.

$R_1$=hydrogen, $R_2$ and $R_3$ form a double bond, $R_4$=6-fluoro, $R_5$=hydrogen, $R_6$ and $R_8$ form a double bond, $R_7$=methyl, $R_9$=hydrogen, $R_{10}$=3-methoxy , $R_{11}$=4-methoxy, and $R_{12}$=5-methoxy.

EXAMPLE 29 rac-ribo-(E)-1-Triazolo-[2',3':1",3"]-1-(butan-1',4'-olido)-[3',4':1,2]-6-fluoro-2-methyl-3-(methylsulfonylbenzylidene)-indan A solution of rac-(E)-1-(2'-Buten-1',4'-olido)-[3',4':1,2]-6-fluoro-2-methyl-3-(p-methylsulfonylbenzylidene)-indan (see Example 3) (1.0 g, 2.69 mmol) in DMF (30ml) is combined with a mixture of $NaN_3$ (0.4 g, 6.15 mmol) in DMF (30 ml) and glacial acetic acid (5 ml). After 4 days at room temperature the reaction mixture is added dropwise to stirred ice-water (800 ml). A white precipitate is filtered off, is washed with water (200 ml), and is recrystallized from MeOH, to give white crystals of rac-ribo-(E)-1-Triazolo-[2', 3':1",3"]-1-(butan-1',4'-olido)-[3',4':1,2]-6-fluoro-2-methyl-3-(methylsulfonylbenzylidene)-indan (0.93 g, 2.25 mmol, 84%). $C_{20}H_{16}FN_3O_4S$:413.42; mp. 185° C.

$R_1$ =hydrogen, $R_2$ and $R_3$ form a triazole, $R_4$=6-fluoro, $R_5$=hydrogen, $R_6$ and $R_8$ form a double bond, $R_7$=methyl, $R_9$, $R_{10}$ and $R_{11}$=hydrogen, and $R_{12}$ =methylsulfonyl.

EXAMPLE 30 rac-threo-(E)-1-N,N-Diethylamino-1-(butan-1',4'-olido)-[3',4':1,2]-6-fluoro-2-methyl-3-(p)-methylsulfonylbenzylidene)-indan rac-(E)-1-(2'-Buten-1',4'-olido)-[3',4':1,2]-6-fluoro-2-methyl-3-(p-methylsulfonylbenzylidene)-indan (see Example 3) (1.0 g, 2.69 mmol) in DMSO (2 ml) reacts with $HNEt_2$ (2 ml) for 3 weeks at room temperature. The excess of $HNEt_2$ is removed in vacuo, and the DMSO solution is added dropwise to stirred ice-water (200 ml). A light yellow solid is filtered off, is washed with water (50 ml), and is purified by flash chromatography ($CH_2Cl_2$) to give rac-threo-(E)-1-N,N-Diethylamino-1-(butan-1',4'-olido)-[3', 4':1,2]-6-fluoro-2-methyl-3-(p-methylsulfonylbenzylidene)-indan. (0.23 g, 0.50 mmol, 19%). $C_{25}H_{28}FNO_4S$:457.56; mp. 208° C.

$R_1$=hydrogen, $R_2$=hydrogen, $R_3$=diethylamino, $R_4$=6-fluoro, $R_5$=hydrogen, $R_6$ and $R_8$ form a double bond, $R_7$=methyl, $R_9$, $R_{10}$ and $R_{11}$=hydrogen, and $R_{12}$=methylsulfonyl.

EXAMPLE 31 rac-threo-(E-)1-(butan-1',4'-olido)-[3',4':1,2]-6-fluoro-2-methyl -3-(p-methylsulfonylbenzylidene)-1S-indanyl-mercaptoacetic acid A mixture of rac-(E)-1-(2'-Buten-1',4'-olido)-[3',4':1,2]-6-fluoro-2-methyl-3-(p-methylsulfonylbenzylidene)-indan (see Example 3) (1.0 g, 2.69 mmol) and mercaptoacetic acid (0.21 ml, 3 mmol) in $CH_3CN$ (30 ml) / aq. 5% $NaHCO_3$ (20 ml) is stirred under $N_2$ for 24 h, at room temperature. The organic solvent is evaporated, and the remaining water phase is added slowly into stirred ice-HCl (200 ml, 10%). The precipitate is filtered off, is washed with water (100 ml), and is recrystallized from $CHCl_3$/n-hexane to give, as white crystals rac-threo-(E)-1-(butan-1',4'-olido)-[3',4':1,2]-6-fluoro-2-methyl-3-(p-methylsulfonylbenzylidene)-1S-indanyl-mercaptoacetic acid (1.1 g, 2.38 mmol, 88%). $C_{22}H_{19}FNO_6S_2$:462.50; mp. 124° C.

$R_1$=hydrogen, $R_2$=hydrogen, $R_3$=mercaptoacetic acid[-H], $R_4$=6-fluoro, $R_5$=hydrogen, $R_6$ and $R_8$ form a double bond, $R_7$=methyl, $R_9$, $R_{10}$ and $R_{11}$=hydrogen, and $R_{12}$=methylsulfonyl.

EXAMPLE 32 rac-threo-(E-1-(butan-1',4'-olido)-[3',4':1,2]-6-fluoro-2-methyl 3-(p-methylsulfonylbenzylidene)-1S-indanyl-L-cysteine A mixture of rac-(E)-1-(2'-Buten-1',4'-olido)-[3',4':1,2]-6-fluoro-2-methyl-3-(p-methylsulfonylbenzylidene)-indan (see Example 3) (15 g, 40.50 mmol) and L-cysteine (4.95 g, 40.85 mmol) in $CH_3CN$ (450 ml) / $H_2O$ (75 ml) is stirred under $N_2$ for 10 d, at room temperature. The solvents are evaporated in vacuo. The residue is dissolved in hot MeOH (750 ml). Addition of water (1 L) leads to a white precipitate, which is filtered off, and is washed with water (200 ml) and n-hexane (100 ml) to give rac-threo-(E)-1-(butan-1',4'-olido) -[3',4':1,2]-6-fluoro-2-methyl-3-(p-methylsulfonylbenzylidene)-1S-indanyl-L-cysteine. (18.3 g, 37.23 mmol, 91%). $C_{23}H_{22}FNO_6S_2$:491.54; mp. 160° C.

$R_1$=hydrogen, $R_2$=hydrogen, $R_3$=cysteine|-H|, $R_4$=6-fluoro, $R_5$=hydrogen, $R_6$ and $R_8$ form a double bond, $R_7$=methyl, $R_9$, $R_{10}$ and $R_{11}$=hydrogen, and $R_{12}$=methylsulfonyl.

EXAMPLE 33 rac-threo-(E)-1-(butan-1',4'-olido)-[3',4':1,2]-6-fluoro-2-methyl -3-(p-methylsulfonylhenzylidene)-1 S-indanyl-N-acetylcysteine A mixture of rac-(E)-1-(2'-Buten-1',4'-olido)-[3',4':1,2]-6-fluoro-2-methyl-3-(p-methylsulfonylbenzylidene)-indan (see Example 3) (20 g, 54 mmol) in $CH_3CN$ (650 ml), with a solution of N-Acetyl-L-cysteine (8.8 g, 53.92 mmol) / $NaHCO_3$ (6.6 g, 78.56 mmol) in water (100 ml) is stirred under $N_2$ for 14 d, at room temperature. The reaction mixture is concentrated (→150 ml) in vacuo and slowly added to crushed ice/HCl (1 L, 10%). A white precipitate is filtered off, and is washed with water (200 ml) and n-hexane (100 ml) to give rac-threo-(E)-1-(butan-1',4'-olido)-[3',4':1, 2]-6-fluoro-2-methyl-3-(p-methylsulfonylbenzylidene)-1S-indanyl-N-acetylcysteine. (27.08 g, 50.75 mmol, 94%). $C_{25}H_{24}FNO_7S_2$:533.58; mp. 137° C.

$R_1$=hydrogen, $R_2$=hydrogen, $R_3$=N—Ac-cysteine|-H|, $R_4$=6-fluoro, $R_5$=hydrogen, $R_6$ and $R_8$ form a double bond, $R_7$=methyl, $R_9$, $R_{10}$ and $R_{11}$=hydrogen, and $R_{12}$=methylsulfonyl.

EXAMPLE 34 rac-threo-(E-1-(butan-1',4'-olido)-[3',4':1,2]-6-fluoro-2-methyl -3-(p-methylsulfonylbenzylidene)-1S-indanyl-glutathione A suspension of rac-(E)-1-(2'-Buten-1',4'-olido)-[3',4':1, 2]-6-fluoro-2-methyl-3-(p-methylsulfonylbenzylidene)-indan (see Example 3) (1.0 g, 2.69 mmol) and glutathione (0.92 g, 2.50 mmol) in $CH_3CN$ / $H_2O$ (30 ml, 2:1) is stirred under $N_2$ for 7 d, at room temperature. The resulting solution is evaporated to dryness. The residue is dried azeotropically with toluene (3×20 ml). The excess of indane starting material is extracted with boiling acetone. A white solid is filtered off, is washed with acetone, and is dried, to give rac-threo-(E)-1-(butan-1',4'-olido)-[3',4':1,2]-6-fluoro-2-methyl-3-(p-methylsulfonylbenzylidene)-1S-indanyl-glutathione (1.68 g, 2.49 mmol, 98%). $C_{30}H_{32}FNO_{10}S_2$:677.73; mp. 150° C. (dec.).

$R_1$=hydrogen, $R_2$=hydrogen, $R_3$=glutathione|-H|, $R_4$=6-fluoro, $R_5$=hydrogen, $R_6$ and $R_8$ form a double bond, $R_7$=methyl, $R_9$, $R_{10}$ and $R_{11}$=hydrogen, and $R_{12}$=methylsulfonyl.

EXAMPLE 35 rac-threo-3-(Butan-1',4'-olido)-[3',4':3,2]-3-bromo-1-(4-chlorobenzoyl -5-methoxy-2-methyl-2,3-dihydroindole (A) 2-methyl-5-methoxy-3-indolylacetic anhydride Dicyclohexylcarbodiimide (10 g, 0.049 mole) is dissolved in a solution of 2-methyl-5-methoxy-3-indolylacetic acid (22 g, 0.10 mole) in 200 ml. of THF, and the solution is allowed to stand at room temperature for 2 hours. The precipitated urea is removed by filtration, and the filtrate is evaporated in vacuo to a residue and flushed with Skellysolve B. The residual oily anhydride is used without purification in the next step.

(B) t-Butyl 2-methyl-5-methoxy-3-indolylacetate t-Butyl alcohol (25 ml.) and fused zinc chloride (0.3 g.) are added to the anhydride from part A. The solution is refluxed for 16 hours and excess alcohol is removed in vacuo. The residue is dissolved in ether, washed several times with saturated bicarbonate, water, and saturated salt solution. After drying over magnesium sulfate, the solution is treated with charcoal, evaporated, and flushed several times with Skellysolve B for complete removal of alcohol. The residual oily ester (18 g., 93%) is used without purification.

(C) t-Butyl 1-p-chlorobenzoyl-2-methyl-5-methoxy-3-indolylacetate

A stirred solution of ester (18 g., 0.065 mole) in dry DMF (450 ml.) is cooled to 4° in an ice bath, and sodium hydride (4.9 g., 0.098 mole, 50% susp.) is added in portions. After 15 minutes, p-chlorobenzoyl chloride (15 g., 0.085 mole) is added dropwise during 10 minutes, and the mixture is stirred for 9 hours without replenishing the ice bath. The mixture is then poured into 1 l of 5% acetic acid, extracted with a mixture of ether and benzene, washed thoroughly with water, bicarbonate, saturated salt, dried over magnesium sulfate, treated with charcoal, and evaporated to a residue which partly crystallizes. This is shaken with ether, filtered, and the filtrate is evaporated to a residue (17 g.) which solidifies after being refrigerated overnight. The crude product is boiled with 300 ml. of Skellysolve B, cooled to room temperature, decanted from some gummy material, treated with charcoal, concentrated to 100 ml., and allowed to crystallize. The product thus obtained (10 g.) is recrystaaazed from 50 ml of methanol and gives 4.5 g. of analytically pure material, M.P. 103°–4°.

(D) 1-p-chlorobenzoyl-2-methyl-5-methoxy-3-indolylacetic acid

A mixture of 1 g. ester and 0.1 g. powdered porous plate is heated in an oil bath at 210° with magnetic stirring under a blanket of nitrogen for about 2 hours. No intensification of color (pale yellow) occurs during this period. After cooling under nitrogen, the product is dissolved in benzene and ether, filtered, and extracted with bicarbonate. The aqueous solution is filtered with suction to remove ether, neutralized with acetic acid, and then acidified weakly with dilute hydrochloric acid. The crude product (0.4 g., 47%) is recrystalized from aqueous ethanol and dried in vacuo at 65°; M.P. 151°.

(E) rac-threo-3-(Butan-1',4'-olido)-[3',4':3,2]-3-bromo-1-(4-chlorobenzoyl)-5-methoxy-2-methyl-2, 3-dihydroindole When 1-(p-chlorobenzoyl)-5-methoxy-2-methylindole-3-acetic acid is allowed to react according to the procedure of Example 2, one obtains rac-threo-3-(Butan-1',4'-olido)-[3', 4':3,2]-3-bromo-1-(4-chlorobenzoyl)-5-methoxy-2-methyl-2,3-dihydroindole. (14.49 g, 33.20 mmol, 83%). $C_{19}H_{15}BrClNO_4$:436.68; mp. 110° C. (dec.).

$R_1$=hydrogen, $R_2$=hydrogen, $R_3$=bromo, $R_5$=S-methoxy, $R_5$=hydrogen, $R^6$-X =nitrogen, $R_8$—C—$R_9$=carbonyl, $R_7$=methyl, $R_{10}$ and $R_{11}$=hydrogen, and $R_{12}$=chloro.

EXAMPLE 36 rac-3-(2'-Buten-1',4'-olido)[3',4':3,2]-1-(4-chlorobenzoyl)-5-methoxy-2-methyl-2,3-dihydroindole rac-threo-3-(Butan-1',4'-olido)-[3',4':3,2]-3-bromo-1-(4-chlorobenzoyl)-5-methoxy-2-methyl-2,3-dihydroindole from Example 35 reacts with N,N-diisopropylethylamine according to the procedure of Example 4 to give rac-3-(2'-Buten-1',4'-olido)-[3',4':3,2]-1-(4-chlorobenzoyl)-5-methoxy-2-methyl-2,3-dihydroindole. (9.35 g, 26.28 mmol, 91%). $C_9H_{14}ClNO_4$:355.77; mp. 169° C.

$R_1$=hydrogen, $R_2$ and $R_3$ form a double bond, $R_4$=5-methoxy, $R_5$=hydrogen, $R^6$-X =nitrogen, $R_8$—C—$R_9$=carbonyl, $R_7$=methyl, $R_{10}$ and $R_{11}$=hydrogen, and $R_{12}$=chloro.

EXAMPLE 37 rac-threo-3-(Butan-1',4'-olido)-[3',4':3,2]-3-(N,N'-diethylaminoethanethio)-1-(4-chlorobenzoyl)-5-methoxy-2-methyl- 2,3-dihydroindole rac-3-(2'-Buten-1',4'-olido)-[3',4':3,2]-1-(4-chlorobenzoyl)-5-methoxy-2-methyl-2,3-dihydroindole from Example 36 reacts with 2-diethylaminoethanethiol x HCl according to the procedure of Example 12 to give rac-threo-3-(Butan-1',4'-olido)-[3',4':3,2]-3-(N,N'-diethylaminoethanethio)-1-(4-chlorobenzoyl)-5-methoxy-2-methyl-2,3-dihydroindole. $C_{25}H_{29}ClN_2O_4$:489.01; mp. 101° C.

$R_1$=hydrogen, $R_2$=hydrogen, $R_3$=S—$CH_2CH_2$—N(Et)$_2$, $R_4$=5-methoxy, $R_5$=hydrogen, $R^6$-X =nitrogen, $R_8$—C—$R_9$=carbonyl, $R_7$=methyl, $R_{10}$ and $R_{11}$=hydrogen, and $R_{12}$=chloro.

Biological Effects

The compounds of this invention were assayed for their effect on various cell lines representative of precancerous lesions to ascertain the degree of tumor growth inhibition following treatment with compounds of this invention. The cell lines employed for these experiments were well characterized, and are used by the United States National Cancer Institute in their screening program for new anticancer drugs. Growth inhibition of this cell line is thought to be indicative of a benefit on precancerous lesions and neoplasms.

Tumor cell cytotoxicity was assessed using the Sulforhodamine B Assay. In this assay, tumor cells were plated in 96-well plates and treated with drug-containing media for seven days (continuous exposure). At the end of the exposure period, the cells were fixed and stained with sulforhodamine B (a pink fluorescent dye). The dye was then solubilized, and the optical density of the resulting pink solution determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent of control" value then represents the degree of growth inhibition caused by the drug.

For each experiment, an $IC_{50}$ value was determined and used for comparative purposes. This value is equivalent to the concentration of drug needed to inhibit tumor cell growth by 50%. $IC_{50}$ values were obtained graphically by connecting the mean values for each drug concentration tested. Each experiment included at least six wells per drug concentration. Concentration was plotted on a log scale on the X-axis. $IC_{50}$ values obtained for the compounds of Examples 1 and 3 are provided in Table I below for several cell lines.

TABLE I

| Cell Line | Type | I.C.$_{50}$ Values (μM) Example 1 | I.C.$_{50}$ Values (μM) Example 3 |
|---|---|---|---|
| HT-29 | Human Colonic Adenocarcinoma-moderately well defined | 0.48 | 0.28 |
| MCF7/S | Human Breast Adenocarcinoma | | 0.20 |
| A427 | Human Lung Adenocarcinoma | | 0.31 |
| UACC375 | Human Melanoma Adenocarcinoma | | 0.35 |

$IC_{50}$ values for other compounds of this invention for the HT-29p136 cell line (a human colonic adenocarcinoma) are listed in Table II below.

TABLE II

| EXAMPLE | IC$_{50}$ (μM) | CELL LINE |
|---|---|---|
| 2 | 0.081 | HT-29 p 135 |
| 4 | 0.11 | HT-29 p 135 |
| 5 | 0.31 | HT-29 p 133 |
| 6 | 27. | HT-29 p 133 |
| 7 | 26. | HT-29 p 133 |
| 8 | 78. | HT-29 p 133 |
| 9 | 110. | HT-29 p 135 |
| 11 | 100. | HT-29 p 135 |
| 12 | 0.39 | HT-29 p 133 |
| 13 | >50. | HT-29 p 136 (?) |
| 27 | 0.34 | HT-29 |
| 28 | 0.28 | HT-29 |
| 29 | 2.4 | HT-29 |
| 30 | 0.35 | HT-29 |
| 31 | 50 | HT-29 |
| 32 | 2.1 | HT-29 |
| 33 | 30 | HT-29 |
| 34 | 3.6 | HT-29 |
| 36 | 2 | HT-29 |
| 37 | 29 | HT-29 |

Compounds of this invention, as well as several others (see Table II below), were evaluated to determine whether they inhibited the production of prostaglandin $E_2$ (PGE$_2$), according to the procedure below. Briefly, the procedure employs HL-60, human promyelocytes, which are differentiated with DMSO in mature granulocytes (Collins, S. J., Ruscetti, F. W., Gallagher, R. E. and Gallo, R. C. (1979) Normal functional characteristics of cultured human promyelocytic leukemia cells (HL-60) after induction of differentiation by dimethylsulfoxide , *J. Exp. Med.* 149:969–974). These differentiated cells produce PGE$_2$ after stimulation with a calcium ionophore A23187 (Kargman, S., Prasit, P. and Evans, J. F. (1991) Translocation of HL-60 cell 5-lipoxygenase. *J. Biol. Chem.* 266: 23745–23752). Secreted PGF$_2$ is measured using an enzyme immunoassay (EIA) kit.

Specifically, HL-60 is a human promyelocytic cell line which may be differentiated in mature granulocytes in the presence of compounds such as dimethyl sulfoxide (DMSO). These cells are obtained from the American Type Culture Collection (ATCC:CCL240). They are grown in a RPM'1640 medium supplemented with 20% heat-inactivated fetal bovine serum, 50 U/ml penicillin and 50

μg/ml streptomycin in an atmosphere of 5% $CO_2$ at 37° C. To induce myeloid differentiation, cells are exposed to 1.3% DMSO for 9 days and then washed and resuspended in Dulbecco's phosphate-buffered saline at $3 \times 10^6$ cells/ml.

The differentiated HL-60 cells ($3 \times 10^6$ cells/ml) are incubated for 15 min at 37° C. in the presence of the compounds listed in Table II at the desired concentration. Cells are then stimulated by A23187 ($5 \times 10^{-6}$M) for 15 min. Secreted $PGE_2$ into the external medium is measured by EIA using a commercially available EIA kit.

The quantity of $PGE_2$ secreted is expressed in $ng/10^6$ cells using a standard curve. Data are converted using a curve fitting of the four parameter logistic equation:

$$f(x) = \frac{a-d}{1+\left(\frac{x}{c}\right)^b} + d$$

Results, expressed as the present of control, are the mean ±s.e.m. of n=3 independent measurements. The $IC_{50}$ values are determined using Hill equation. The effects of the tested compounds on $PGE_2$ production by human granulocytes are shown in Table III.

Indomethacin inhibits $PGE_2$ production with an $IC_{50}$ value of 2nM in accordance with this standard. The sulfone inhibits $PGE_2$ production only at relatively high concentrations: the $IC_{50}$ value is 100μM. The compounds sulindac sulfide and Example 3 above, studied at $10^{-5}$M, inhibit $PGE_2$ production by 100% and 79% respectively.

TABLE III

| Drug | (Anti-proliferative activity) HT-29 I.C.$_{50}$ (μM) | (Anti-PG Synthetase activity) $PGE_2$ I.C.$_{50}$ (μM) | SELECTIVITY INDEX (HT-29 $IC_{50}$/ $PGE_2$ $IC_{50}$) |
|---|---|---|---|
| Sulfone | 119 | 100 | 1.19 |
| Sulindac Sulfide | 64 | 0.05 | 1,280 |
| Indomethacin | 66 | 0.002 | 33,000 |
| Diclofenac | 55 | 0.001 | 55,000 |
| Salicylic Acid | 2333 | 0.3 | 7,776 |
| Ibuprofen | 520 | 0.2 | 2,600 |
| Example 3 | 0.28 | 40 | 0.007 |
| Example 12 | 0.43 | >100 | <0.0043 |
| Example 29 | 2.4 | 1.5 | 1.6 |
| Example 30 | 0.35 | >100 | <0.0035 |
| Example 34 | 3.6 | >100 | <0.036 |
| Example 36 | 2 | 0.08 | 25 |

Given that high levels of anti-PG synthetase activity are associated with undesirable side-effects (e.g., gastric irritation and ulceration), the ratios of antiproliferative activity to anti-PG synthetase activity (i.e. the "selectivity index" referred to in Table II) is important. Lower selectivity indices provide greater opportunities for administering therapeutic levels of compound while minimizing the risk of gastrointestinal side-effects. For example, the sulindac sulfide, which has good anti-proliferative activity ($IC_{50}$= 44μm), unfortunately manifests a high degree of anti-PG-synthetase activity which precludes safe, long-term treatment for pre-cancerous lesions. In marked contrast, the compounds of this invention (as exemplified by the compound of Example 3 in Table II) has outstanding antiproliferative activity while essentially lacking anti-prostaglandin activity at therapeutic concentrations. Compounds of this invention, therefore, are excellent candidates for long term use as therapeutic agents for precancerous lesions.

The compounds of this invention can be formulated with pharmaceutically acceptable carriers into unit dosage forms in a conventional manner so that the patient in need of therapy for precancerous lesions can periodically (e.g. once or more per day) take a compound according to the method of this invention.

The exact initial dose of the compounds of this invention can be determined with reasonable experimentation, but is believed to be between 0.375 mg/day to 5 mg/day in the average adult.

It will be understood that various changes and modifications can be made in the details of procedure, formulation and use without departing from the spirit of the invention, especially as defined in the following claims.

We claim:

1. A compound comprising:

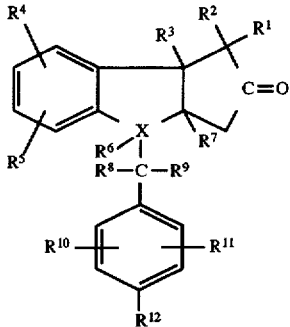

wherein X is selected from the group consisting of carbon or nitrogen; when X is nitrogen, $R^6$ is absent;

$R_1$ and $R_2$ are independently selected from the group consisting of hydrogen, amino, lower alkyl, lower alkoxy, azide, hydroxy, halogen, acetoxyl, benzoxy, or substituted phenyl where the substituents are selected from the group consisting of halogen, lower alkyl, or lower alkoxy; or $R_1$ and $R_2$ form a carbonyl or imine; or $R_2$ and $R_3$ together form a double bond, aziridin, epoxide or triazole; or a dioxolane;

$R_3$ is selected from the group consisting of hydrogen, halogen, azide, lower alkoxy, cyano, hydroxy, di(lower)alkyl amino(lower)alkylthio, loweralkylthio, phenylthio, or di(lower) alkylamino; or, $R_3$ is further selected from a group consisting of mercaptoacetic acid, cysteine, N-Ac-cysteine and glutathione;

$R_4$ is selected from the group consisting of hydrogen, hydroxy, halogen, lower alkoxy or lower alkyl, or lower dialkyl amino;

$R_5$ is selected from the group consisting of hydrogen, hydroxy, halogen, lower alkoxy, lower alkyl, amino, or lower dialkyl amino;

$R_6$ is selected from the group consisting of hydrogen, lower alkyl, hydroxy, lower alkoxy, halogen or $R_6$ and $R_8$ together form a double bond;

$R_7$ is selected from the group consisting of hydrogen, lower alkyl, phenyl, halo(lower)alkyl, hydroxy(lower) alkyl, acetoxy(lower)alkyl, benzyloxy(lower)alkyl, or (lower)alkyl(lower)alkoxy, or di(lower)alkylamiino (lower)alkyl;

$R_8$ and $R_9$ are independently selected from the group consisting of hydrogen, lower alkyl, hydroxy, lower alkoxy, or halogen; or $R_9$ and $R_9$ together may be oxygen;

$R_{10}$ and $R_{11}$, are independently selected from the group consisting of hydrogen, halogen, lower alkoxy, or lower alkyl; and $R_{12}$ is selected from the group consisting of hydrogen, halogen, lower alkyl, lower alkoxy, lowerkylthio, loweralkylsulfinyl, lower alkyl sulfonyl, or amidosulfonyl.

2. The compound of claim 1 where X is nitrogen.

3. The compound of claim 2 wherein $R_1$ and $R_2$ are independently selected from the group consisting of hydrogen, amino, lower alkyl, lower alkoxy, azide, hydroxy, or halogen, or $R_1$ and $R_2$ form a carbonyl; or $R_2$ and $R_3$ form a double bond, aziridin, epoxide, triazole or dioxolane;

$R_4$ and $R_5$ are independently selected from the group consisting of hydrogen, halogen or lower alkoxy;

$R_7$ is selected from the group consisting of hydrogen, lower alkyl, halo(lower)alkyl, hydroxy(lower)alkyl, acetoxy(lower)alkyl, benzyloxy(lower)alkyl, or (lower)alkyl(lower)alkoxy;

$R_8$ and $R_9$ together are an oxygen; and $R_{10}$–$R_{11}$ are hydrogen.

4. The compound of claim 1 wherein X is carbon.

5. The compound of claim 4 wherein $R_1$ and $R_2$ are independently selected from the group consisting of hydrogen, amino, lower alkyl, lower alkoxy, azide, hydroxy, or halogen, or $R_1$ and $R_2$ form a carbonyl; or $R_2$ and $R_3$ form a double bond, aziridin, epoxide, triazole or dioxolane;

$R_4$ and $R_5$ are independently selected from the group consisting of hydrogen, halogen or lower alkoxy;

$R_6$ is hydrogen or together with $R_8$ forms a double bond;

$R_7$ is selected from the group consisting of hydrogen, lower alkyl, halo(lower)alkyl, hydroxy(lower)alkyl, acetoxy(lower)alkyl, benzyloxy(lower)alkyl, or (lower)alkyl(lower)alkoxy; and $R_8$–$R_{11}$ are hydrogen.

6. The compound of claim 5 wherein $R_4$ and $R_5$ are independently selected from the group consisting of hydrogen and halogen.

7. The compound of claim 6 wherein $R_{12}$ is lower alkyl sulfonyl.

8. The compound of claim 6 wherein $R_4$ is halogen and $R_5$ is hydrogen.

9. The compound of claim 8 wherein $R_7$ is lower alkyl.

10. The compound of claim 5 wherein the compound is rac-(E)-1-Triozolo-[2',3':1,3"]-1-(butan-1',4'-olido)-[3',4':1,2]-6-fluoro-2-methyl-3-(methylsulfonylbenzylidene)-indan.

11. The compound of claim 5 wherein the compound is rac-(E)-1-(N,N'-diethylaminoethanethio)-1-(butan-1',4'-olido)-[3',4':1,2]-6-fluoro-2-methyl-3-(p-methylsulfonylbenzylidene)-indan.

12. The compound of claim 5 wherein the compound is rac-(E)-1-bromo-1-(butan-1',4'-olido)-[3',4':1,2]-6-fluoro-2-methyl-3-(p-methylsulfonylbenzylidene)-indan.

13. A method of treating a patient having precancerous lesions in need of treatment, comprising administering to the patient a physiologically effective amount of a compound of the formula:

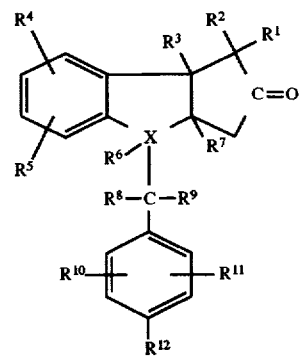

wherein X is selected from the group consisting of carbon and nitrogen; when X is nitrogen $R^6$ is absent;

$R_1$ and $R_2$ are independently selected from the group consisting of hydrogen, amino, lower alkyl, lower alkoxy, azide, hydroxy, halogen, acetoxyl, benzoxy, or phenyl or substituted phenyl where the substituents are selected from the group consisting of halogen, lower alkyl, or lower alkoxy; or $R_1$ and $R_2$ form a carbonyl or imine; or $R_2$ and $R_3$ together form a double bond, aziridin, epoxide or triazole; or a dioxolane;

$R_3$ is selected from the group consisting of hydrogen, halogen, azide, lower alkyl, lower alkoxy, cyano, hydroxy, di(lower)alkyl amino(lower)alkylthio, loweralkylthio, phenylthio, di(lower) alkylamino, or from a group consisting of mercaptoacetic acid cysteine N—Ac-cysteine and glutathione;

$R_4$ is selected from the group consisting of hydrogen, hydroxy, halogen, lower alkoxy or lower alkyl, or lower dialkyl amino;

$R_5$ is selected from the group consisting of hydrogen, hydroxy, halogen, lower alkoxy, lower alkyl, amino, or lower dialkyl amino;

$R_6$ is selected from the group consisting of hydrogen, lower alkyl, hydroxy, lower alkoxy, halogen or $R_6$ and $R_8$ together from a double bond;

$R_7$ is selected from the group consisting of hydrogen, lower alkyl, phenyl, halo(lower)alkyl, hydroxy(lower)alkyl, acetoxy(lower)alkyl, benzyloxy(lower)alkyl, or (lower)alkyl(lower)alkoxy, or di(lower)alkylamino (lower)alkyl;

$R_8$ and $R_9$ are independently selected from the group consisting of hydrogen, lower alkyl, hydroxy, lower alkoxy, or halogen;

$R_{10}$ and $R_{11}$ are independently selected from the group consisting of hydrogen, halogen, lower alkoxy, or lower alkyl; and $R_{12}$ is selected from the group consisting of hydrogen, halogen, lower alkyl, lower alkoxy, loweralkylthio, loweralkylsulfinyl, lower alkyl sulfonyl, or amidosulfonyl.

14. The method of claim 13 wherein X is nitrogen.

15. The method of claim 14 wherein $R_1$ and $R_2$ are independently selected from the group consisting of hydrogen, amino, lower alkyl, lower alkoxy, azide, hydroxy, or halogen, or $R_1$ and $R_2$ form a carbonyl; or $R_2$ and $R_3$ form a double bond, aziridin, epoxide, triazole or dioxolane;

$R_4$ and $R_5$ are independently selected from the group consisting of hydrogen, halogen or lower alkoxy;

$R_7$ is selected from the group consisting of hydrogen, lower alkyl, halo(lower)alkyl, hydroxy(lower)alkyl, acetoxy(lower)alkyl, benzyloxy(lower)alkyl, or (lower)alkyl(lower)alkoxy;

$R_8$ and $R_9$ together are an oxygen; and $R_{10}$ and $R_{11}$ are hydrogen.

16. The method of claim 13 wherein X is carbon.

17. The method of claim 16 wherein $R_1$ and $R_2$ are independently selected from the group consisting of hydrogen, amino, lower alkyl, lower alkoxy, azide, hydroxy, or halogen, or $R_1$ and $R_2$ form a carbonyl; or $R_2$ and $R_3$ form a double bond, aziridin, epoxide, triazole or dioxolane;

$R_4$ and $R_5$ are independently selected from the group consisting of hydrogen, halogen or lower alkoxy;

$R_6$ is hydrogen or together with $R_8$ forms a double bond;

$R_7$ is selected from the group consisting of hydrogen, lower alkyl, halo(lower)alkyl, hydroxy(lower)alkyl, acetoxy(lower)alkyl, benzyloxy(lower)alkyl, or (lower)alkyl(lower)alkoxy; and $R_8$–$R_1$, are hydrogen.

18. The method of claim 17 wherein $R_4$ and $R_5$ are independently selected from the group consisting of hydrogen and halogen.

19. The method of claim 18 wherein $R_{12}$ is lower alkyl sulfonyl.

20. The method of claim 18 wherein $R_4$ is halogen and $R_5$ is hydrogen.

21. The method of claim 20 wherein $R_7$ is lower alkyl.

22. The method of claim 16 wherein said compound is rac-ribo-(E)-1-triazolo-1-(butan-1',4'-olido)-[3',4':1,2]-6-fluoro-2-methyl-3-(methylsulfonylbenzylidene)-indan.

23. The method of claim 16 wherein said compound is rac-(E)-1-(N,N'-diethylaminoethanethio)-1-(butan-1',4'-olido)-[3',4':1,2]-6-fluoro-2-methyl-3-(p-methylsulfonylbenzylidene)-indan.

24. A method for inhibiting the growth of neoplastic cells comprising exposing said cells to an effective amount of a compound of the formula:

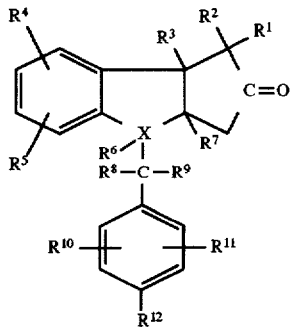

X is selected from the group consisting of carbon and nitrogen; when X is nitrogen $R^6$ is absent;

$R_1$ and $R_2$ are independently selected from the group consisting of hydrogen, amino, lower alkyl, lower alkoxy, azide, hydroxy, halogen, acetoxyl, benzoxy, or phenyl or substituted phenyl where the substituents are selected from the group consisting of halogen, lower alkyl, or lower alkoxy; or $R_1$ and $R_2$ from a carbonyl or imine; or $R_2$ and $R_3$ together form a double bond, aziridin, epoxide or triazole; or a dioxolane;

$R_3$ is selected from the group consisting of hydrogen, halogen, azide, lower alkyl, lower alkoxy, cyano, hydroxy, di(lower)alkyl amino(lower)alkylthio, loweralkylthio, phenylthio, di(lower)alkylamino, or from a group consisting of mercaptoacetic acid, cysteine, N—Ac-cysteine and glutathione;

$R_4$ is selected from the group consisting of hydrogen, hydroxy, halogen, lower alkoxy or lower alkyl, or lower dialkyl amino;

$R_5$ is selected from the group consisting of hydrogen, hydroxy, halogen, lower alkoxy, lower alkyl, amino, or lower dialkyl amino;

$R_6$ is selected from the group consisting of hydrogen, lower alkyl, hydroxy, lower alkoxy, halogen or $R_6$ and $R_8$ together from a double bond;

$R_7$ is selected from the group consisting of hydrogen, lower alkyl, phenyl, halo(lower)alkyl, hydroxy(lower)alkyl, acetoxy(lower)alkyl, benzyloxy(lower)alkyl, or (lower)alkyl(lower)alkoxy, or di(lower)alkylamino (lower)alkyl;

$R_8$ and $R_9$ are independently selected from the group consisting of hydrogen, lower alkyl, hydroxy, lower alkoxy, or halogen; or $R_8$ and $R_9$ together may be oxygen;

$R_{10}$ and $R_{11}$ are independently selected from the group consisting of hydrogen, halogen, lower alkoxy, or lower alkyl; and $R_{12}$ is selected from the group consisting of hydrogen, halogen, lower alkyl, lower alkoxy, loweralkylthio, loweralkylsulfinyl, lower alkyl sulfonyl, or amidosulfonyl.

25. The method of claim 24 wherein X is nitrogen.

26. The method of claim 25 wherein $R_1$ and $R_2$ are independently selected from the group consisting of hydrogen, amino, lower alkyl, lower alkoxy, azide, hydroxy, or halogen, or $R_1$ and $R_2$ form a carbonyl; or $R_2$ and $R_3$ form a double bond, aziridin, epoxide, triazole or dioxolane;

$R_4$ and $R_5$ are independently selected from the group consisting of hydrogen, halogen or lower alkoxy;

$R_7$ is selected from the group consisting of hydrogen, lower alkyl, halo(lower)alkyl, hydroxy(lower)alkyl, acetoxy(lower)alkyl, benzyloxy(lower)alkyl, or (lower)alkyl(lower)alkoxy;

$R_8$–$R_9$ together are an oxygen; and $R_{10}$–$R_{11}$ are hydrogen.

27. The method of claim 26 wherein $R_1$ is an oxygen and $R_7$ is selected from the group consisting of hydrogen and lower alkyl.

28. The method of claim 24 wherein X is carbon.

29. The method of claim 28 wherein $R_1$ and $R_2$ are independently selected from the group consisting of hydrogen, amino, lower alkyl, lower alkoxy, azide, hydroxy, or halogen, or $R_1$ and $R_2$ form a carbonyl; or $R_2$ and $R_3$ form a double bond, aziridin, epoxide, triazole or dioxolane;

$R_4$ and $R_5$ are independently selected from the group consisting of hydrogen, halogen or lower alkoxy;

$R_6$ is hydrogen or together with $R_8$ forms a double bond;

$R_7$ is selected from the group consisting of hydrogen, lower alkyl, halo(lower)alkyl, hydroxy(lower)alkyl, acetoxy(lower)alkyl, benzyloxy(lower)alkyl, or (lower)alkyl(lower)alkoxy; and $R_8$–$R_{11}$ are hydrogen.

30. The method of claim 29 wherein $R_{12}$ is lower alkyl sulfonyl.

31. A pharmaceutical composition comprising an acceptable pharmaceutical carrier and a compound having the formula below:

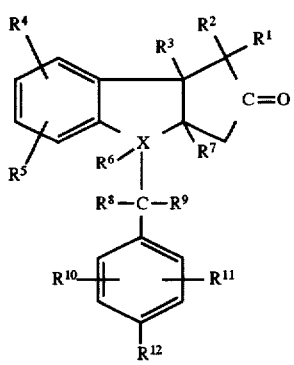

wherein X is selected from the group consisting of carbon or nitrogen; when X is nitrogen, R⁶ is absent;

R₁ and R₂ are independently selected from the group consisting of hydrogen, amino, lower alkyl, lower alkoxy, azide, hydroxy, halogen, acetoxyl, benzoxy, or substituted phenyl where the substituents are selected from the group consisting of halogen, lower alkyl, or lower alkoxy; or R₁ and R₂ form a carbonyl or imine; or R₂ and R₃ together form a double bond, aziridin, epoxide or triazole; or a dioxolane;

R₃ is selected from the group consisting of hydrogen, halogen, azide, lower alkyl, lower alkoxy, cyano, hydroxy, di(lower)alkyl amino(lower)alkylthio, loweralkylthio, phenylthio, or di(lower) alkylamino; or, R₃ is further selected from a group consisting of mercaptoacetic acid, cysteine, N—Ac-cysteine and glutathione;

R₄ is selected from the group consisting of hydrogen, hydroxy, halogen, lower alkoxy or lower alkyl, or lower dialkyl amino;

R₅ is selected from the group consisting of hydrogen, hydroxy, halogen, lower alkoxy, lower alkyl, amino, or lower dialkyl amino;

R₆ is selected from the group consisting of hydrogen, lower alky, hydroxy, lower alkoxy, halogen or R₆ and R₈ together from a double bond;

R₇ is selected from the group consisting of hydrogen, lower alkyl, phenyl, halo(lower)alkyl, hydroxy(lower) alkyl, acetoxy(lower)alkyl, benzyloxy(lower)alkyl, or (lower)alkyl(lower)alkoxy, or di(lower)alkylamino (lower)alkyl;

R₈ and R₉ are independently selected from the group consisting of hydrogen, lower alkyl, hydroxy, lower alkoxy, or halogen; or R₈ and R₉ together may be oxygen;

R₁₀ and R₁₁ are independently selected from the group consisting of hydrogen, halogen, lower alkoxy, or lower alkyl; and R₁₂ is selected from the group consisting of hydrogen, halogen, lower alkyl, lower alkoxy, lowerkylthio, loweralkylsulfinyl, lower alkyl sulfonyl, or amidosulfonyl.

32. The pharmaceutical composition of claim 31 where X is nitrogen.

33. The pharmaceutical composition of claim 32 wherein R₁ and R₂ are independently selected from the group consisting of hydrogen, amino, lower alkyl, lower alkoxy, azide, hydroxy, or halogen, or R₁ and R₂ form a carbonyl; or R₂ and R₃ form a double bond, aziridin, epoxide, triazole or dioxolane;

R₄ and R₅ are independently selected from the group consisting of hydrogen, halogen or lower alkoxy;

R₇ is selected from the group consisting of hydrogen, lower alkyl, halo(lower)alkyl, hydroxy(lower)alkyl, acetoxy(lower)alkyl, benzyloxy(lower)alkyl, or (lower)alkyl(lower)alkoxy;

R₈ and R₉ together are an oxygen; and

R₁₀-R₁₁ are hydrogen.

34. The pharmaceutical composition of claim 30 wherein X is carbon.

35. The pharmaceutical composition of claim 34 wherein R₁ and R₂ are independently selected from the group consisting of hydrogen, amino, lower alkyl, lower alkoxy, azide, hydroxy, or halogen, or R₁ and R₂ form a carbonyl; or R₂ and R₃ form a double bond, aziridin, epoxide, triazole or dioxolane;

R₄ and R₅ are independently selected from the group consisting of hydrogen, halogen or lower alkoxy;

R₆ is hydrogen or together with R₈ forms a double bond;

R₇ is selected from the group consisting of hydrogen, lower alkyl, halo(lower)alkyl, hydroxy(lower)alkyl, acetoxy(lower)alkyl, benzyloxy(lower)alkyl, or (lower)alkyl(lower)alkoxy; and R₈-R₁₁ are hydrogen.

36. The pharmaceutical composition of claim 35 wherein R₄ and R₅ are independently selected from the group consisting of hydrogen and halogen.

37. The pharmaceutical composition of claim 36 wherein R₁₂ is lower alkyl sulfonyl.

38. The pharmaceutical composition of claim 36 wherein R₄ is halogen and R₅ is hydrogen.

39. The pharmaceutical composition of claim 38 wherein R₇ is lower alkyl.

40. The pharmaceutical composition of claim 34 wherein the compound is rac-(E)-1-(Buten-1',4'-olido)-[3',4':1,2]-6-fluoro-2-methyl-3-(p-methylsulfonylbenzylidene)-indan.

41. The pharmaceutical composition of claim 34 wherein the compound is rac-(E)-1-Triozolo-[2',3':1",3"]-1-(butan-1',4'-olido)-[3',4':1,2]-6-fluoro-2-methyl-3-(methylsulfonylbenzylidene)-indan.

42. The pharmaceutical composition of claim 34 wherein the compound is rac-(E)-1-(N,N'-diethylaminoethanethio)-1-(butan-1',4'-olido)-[3',4':1,2]-6-fluoro-2-methyl-3 -(p-methylsulfonylbenzylidene)-indan.

43. The pharmaceutical composition of claim 34 wherein the compound is rac-(E)-1-bromo-1-(butan-1',4'-olido)-[3',4':1,2]-6-fluoro-2-methyl-3-(p-methylsulfonylbenzylidene)-indan.

* * * * *